US010780083B1

(12) United States Patent
Cole et al.

(10) Patent No.: US 10,780,083 B1
(45) Date of Patent: *Sep. 22, 2020

(54) CHARGED ION CHANNEL BLOCKERS AND METHODS FOR USE

(71) Applicant: Nocion Therapeutics, Inc., Cambridge, MA (US)

(72) Inventors: Bridget McCarthy Cole, Quincy, MA (US); James Lamond Ellis, Somerville, MA (US)

(73) Assignee: Nocion Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/675,982

(22) Filed: Nov. 6, 2019

Related U.S. Application Data

(60) Provisional application No. 62/816,434, filed on Mar. 11, 2019.

(51) Int. Cl.
| | | |
|---|---|---|
| *A61K 31/40* | (2006.01) | |
| *A61K 31/4453* | (2006.01) | |
| *A61K 31/55* | (2006.01) | |
| *A61P 29/00* | (2006.01) | |
| *C07D 207/04* | (2006.01) | |
| *C07D 211/06* | (2006.01) | |
| *C07D 223/02* | (2006.01) | |
| *C07D 225/02* | (2006.01) | |
| *A61K 31/452* | (2006.01) | |
| *C07D 211/14* | (2006.01) | |
| *C07D 207/06* | (2006.01) | |
| *A61K 45/06* | (2006.01) | |
| *C07D 223/04* | (2006.01) | |
| *A61K 31/395* | (2006.01) | |

(52) U.S. Cl.
CPC ............ *A61K 31/452* (2013.01); *A61K 31/40* (2013.01); *A61K 31/55* (2013.01); *A61K 31/5545* (2017.08); *A61K 45/06* (2013.01); *C07D 207/06* (2013.01); *C07D 211/14* (2013.01); *C07D 223/04* (2013.01); *C07D 225/02* (2013.01)

(58) Field of Classification Search
CPC .... A61K 31/40; A61K 31/4453; A61K 31/55; A61K 31/5545; A61P 29/00; C07D 207/04; C07D 211/06; C07D 223/02; C07D 225/02
See application file for complete search history.

(56) References Cited

U.S. PATENT DOCUMENTS

| | | |
|---|---|---|
| 1,889,645 A | 11/1932 | Otto |
| 2,441,498 A | 5/1948 | Loefgren et al. |
| 2,689,248 A | 9/1954 | Clinton et al. |
| 2,759,975 A | 8/1956 | Chiddix |
| 2,774,770 A | 12/1956 | Kerwin |
| 2,783,230 A | 2/1957 | Goldberg |
| 2,799,679 A | 7/1957 | Thuresson et al. |
| 2,955,111 A | 10/1960 | Thuresson et al. |
| 3,049,546 A | 8/1962 | Renner |
| 3,160,662 A | 12/1964 | Magnus et al. |
| 3,177,252 A | 4/1965 | Leon |
| 3,264,309 A | 8/1966 | Zenitz |
| 3,519,631 A | 7/1970 | Jerchel et al. |
| 3,773,939 A | 11/1973 | Janssen |
| 3,812,147 A | 5/1974 | Adams et al. |
| 3,900,481 A | 8/1975 | Banitt et al. |
| 3,931,195 A | 1/1976 | Dykstra et al. |
| 4,069,309 A | 1/1978 | Ciaudelli et al. |
| 4,070,347 A | 1/1978 | Schmitt |
| 4,222,766 A | 9/1980 | Martin |
| 4,233,055 A | 11/1980 | Martin |
| 4,293,539 A | 10/1981 | Ludwig et al. |
| 4,360,465 A | 11/1982 | Buschmann et al. |
| 4,757,128 A | 7/1988 | Domb et al. |
| 4,877,805 A | 10/1989 | Kligman |
| 4,975,282 A | 12/1990 | Cullis et al. |
| 4,980,378 A | 12/1990 | Wong et al. |
| 4,994,213 A | 2/1991 | Aitcheson et al. |
| 5,000,958 A | 3/1991 | Fountain et al. |
| 5,023,087 A | 6/1991 | Yau-Young |
| 5,032,582 A | 7/1991 | Abra |
| 5,049,388 A | 9/1991 | Knight et al. |
| 5,082,866 A | 1/1992 | Wong et al. |
| 5,169,637 A | 12/1992 | Lenk et al. |
| 5,176,907 A | 1/1993 | Leong |
| 5,194,266 A | 3/1993 | Abra et al. |
| 5,194,581 A | 3/1993 | Leong |
| 5,356,633 A | 10/1994 | Woodle et al. |
| 5,409,704 A | 4/1995 | Bally et al. |
| 5,480,971 A | 1/1996 | Houghten et al. |

(Continued)

FOREIGN PATENT DOCUMENTS

| | | |
|---|---|---|
| CA | 982148 | 1/1976 |
| CA | 2717042 | 9/2009 |

(Continued)

OTHER PUBLICATIONS

Cole, Bridget M., et al., U.S. Appl. No. 16/815,803, filed Mar. 11, 2019.
Cole, Bridget M., et al., U.S. Appl. No. 16/815,426, filed Mar. 11, 2019.
Cole, Bridget M., et al., U.S. Appl. No. 16/815,868, filed Mar. 11, 2019.

(Continued)

*Primary Examiner* — Brenda L Coleman

(74) *Attorney, Agent, or Firm* — Elmore Patent Law Group, P.C.; Carolyn S. Elmore; Mahreen Chaudhry Hoda

(57) ABSTRACT

The invention provides compounds of Formula (I), or pharmaceutically acceptable salts thereof. The compounds, compositions, methods and kits of the invention are useful for the treatment of pain, itch, and neurogenic inflammation.

28 Claims, 1 Drawing Sheet

(56) References Cited

U.S. PATENT DOCUMENTS

| | | |
|---|---|---|
| 5,552,155 A | 6/1996 | Jones |
| 5,591,317 A | 1/1997 | Pitts, Jr. |
| 5,688,525 A | 11/1997 | Adler-Moore et al. |
| 5,747,470 A | 5/1998 | Becherer et al. |
| 5,783,683 A | 7/1998 | Morrison |
| 5,874,104 A | 2/1999 | Adler-Moore et al. |
| 5,883,228 A | 3/1999 | Darnell, Jr. et al. |
| 5,952,451 A | 9/1999 | Zhao |
| 6,008,318 A | 12/1999 | Zhao |
| 6,051,576 A | 4/2000 | Ashton et al. |
| 6,083,996 A | 7/2000 | Buyuktimkin et al. |
| 6,103,255 A | 8/2000 | Levene |
| 6,118,020 A | 9/2000 | Buyuktimkin et al. |
| 6,153,212 A | 11/2000 | Mao et al. |
| 6,355,637 B1 | 3/2002 | Axt et al. |
| 6,362,197 B1 | 3/2002 | Page et al. |
| 6,413,961 B1 | 7/2002 | Demopulos et al. |
| 6,432,937 B1 | 8/2002 | Hallgren |
| 6,623,040 B1 | 9/2003 | Foley et al. |
| 6,709,406 B2 | 3/2004 | Laserow |
| 6,766,319 B1 | 7/2004 | Might |
| 6,825,190 B2 | 11/2004 | Moon et al. |
| 6,884,782 B2 | 4/2005 | Huang et al. |
| 7,166,590 B2 | 1/2007 | Seko et al. |
| 7,429,673 B2 | 9/2008 | Morazzoni et al. |
| 7,446,226 B2 | 11/2008 | Helsing et al. |
| 7,705,004 B2 | 4/2010 | Song et al. |
| 8,138,339 B2 | 3/2012 | Bauer et al. |
| 8,143,412 B2 | 3/2012 | Priebe et al. |
| 8,258,144 B2 | 9/2012 | Song et al. |
| 8,273,390 B2 | 9/2012 | Muhammad et al. |
| 8,652,497 B2 | 2/2014 | Sackler |
| 8,822,537 B2 | 9/2014 | Buyuktimkin et al. |
| 9,603,817 B2 | 3/2017 | Bean et al. |
| 10,179,116 B2 | 1/2019 | Bean et al. |
| 2003/0105126 A1 | 6/2003 | Demopulos et al. |
| 2003/0152637 A1 | 8/2003 | Chasin et al. |
| 2003/0166629 A1 | 9/2003 | Choi et al. |
| 2004/0146590 A1 | 7/2004 | Iadarola et al. |
| 2004/0220187 A1 | 11/2004 | Stephenson et al. |
| 2004/0266870 A1 | 12/2004 | Allegretti et al. |
| 2005/0009016 A1 | 1/2005 | Moskowitz et al. |
| 2005/0025765 A1 | 2/2005 | DiMauro et al. |
| 2005/0090557 A1 | 4/2005 | Muhammad et al. |
| 2005/0142596 A1 | 6/2005 | Krolewski et al. |
| 2005/0152957 A1 | 7/2005 | Cleary et al. |
| 2005/0233398 A1 | 10/2005 | Chu et al. |
| 2005/0277680 A1 | 12/2005 | Priebe et al. |
| 2006/0036098 A1 | 2/2006 | Kim et al. |
| 2006/0062739 A1 | 3/2006 | Hofmann et al. |
| 2006/0100272 A1 | 5/2006 | Maniar |
| 2006/0106020 A1 | 5/2006 | Rodgers et al. |
| 2006/0134008 A1 | 6/2006 | Deaver |
| 2006/0183906 A1 | 8/2006 | Rodgers et al. |
| 2007/0135461 A1 | 6/2007 | Rodgers et al. |
| 2007/0149469 A1 | 6/2007 | Korherr |
| 2007/0149506 A1 | 6/2007 | Arvanitis et al. |
| 2007/0197509 A1 | 8/2007 | Babinski et al. |
| 2008/0188500 A1 | 8/2008 | Arvanitis et al. |
| 2008/0312212 A1 | 12/2008 | Collingwood et al. |
| 2009/0054485 A1 | 2/2009 | Gleich et al. |
| 2009/0060898 A1 | 3/2009 | Kandimalla et al. |
| 2009/0162333 A1 | 6/2009 | Pavs et al. |
| 2009/0270478 A1 | 10/2009 | Feddia et al. |
| 2010/0098685 A1 | 4/2010 | Zhu et al. |
| 2010/0099772 A1 | 4/2010 | Bean et al. |
| 2010/0113416 A1 | 5/2010 | Friedman et al. |
| 2010/0120781 A1 | 5/2010 | Neamati |
| 2011/0086818 A1 | 4/2011 | Bean et al. |
| 2012/0022142 A1 | 1/2012 | Jadhav et al. |
| 2012/0129867 A1 | 5/2012 | Bauer et al. |
| 2012/0172429 A1 | 7/2012 | Woolf et al. |
| 2012/0195902 A1 | 8/2012 | Friedman et al. |
| 2015/0087552 A1 | 3/2015 | Jensen et al. |
| 2015/0087714 A1 | 3/2015 | Bean et al. |
| 2017/0319517 A1 | 11/2017 | Bean et al. |
| 2018/0237392 A1 | 8/2018 | Bean et al. |
| 2018/0303945 A1 | 10/2018 | Adams et al. |
| 2019/0216747 A1 | 7/2019 | Woolf et al. |

FOREIGN PATENT DOCUMENTS

| | | |
|---|---|---|
| CH | 311606 | 11/1955 |
| CH | 311607 | 11/1955 |
| CH | 311608 | 11/1955 |
| CH | 311609 | 11/1955 |
| CH | 311610 | 11/1955 |
| CH | 311611 | 11/1955 |
| CH | 311612 | 11/1955 |
| CH | 311613 | 11/1955 |
| CH | 311614 | 11/1955 |
| CH | 311615 | 11/1955 |
| CN | 101156851 | 4/2008 |
| CN | 101347427 A | 1/2009 |
| DE | 150423 A1 | 9/1981 |
| DE | 151036 A1 | 9/1981 |
| DE | 298723 A5 | 3/1992 |
| DE | 298726 A5 | 3/1992 |
| DE | 298727 A5 | 3/1992 |
| DE | 100 39 449 | 7/2003 |
| EP | 0586106 A1 | 3/1994 |
| GB | 751522 A | 6/1956 |
| GB | 756538 A | 9/1956 |
| GB | 895601 | 5/1962 |
| GB | 901377 A | 7/1962 |
| JP | 2000-143635 | 5/2000 |
| RU | 2105554 C1 | 2/1998 |
| RU | 2258700 C1 | 8/2005 |
| WO | 1985/00599 A1 | 2/1985 |
| WO | 1996/40061 A1 | 12/1996 |
| WO | 9704770 A1 | 2/1997 |
| WO | 98/24428 A1 | 6/1998 |
| WO | 1998/37896 A1 | 9/1998 |
| WO | 99/11252 A2 | 3/1999 |
| WO | 99/63985 A1 | 12/1999 |
| WO | 01/44192 A1 | 6/2001 |
| WO | 01/44218 A1 | 6/2001 |
| WO | 01/45678 A1 | 6/2001 |
| WO | 2004/012757 A2 | 2/2004 |
| WO | 2004/110423 A1 | 12/2004 |
| WO | 2005/014849 A2 | 2/2005 |
| WO | 2005/089206 A2 | 9/2005 |
| WO | 2005/117981 A1 | 12/2005 |
| WO | 2006/010587 A1 | 2/2006 |
| WO | 2006/065722 A2 | 6/2006 |
| WO | 2006/133588 A1 | 12/2006 |
| WO | 2007/071055 A1 | 6/2007 |
| WO | 2008/063603 A2 | 5/2008 |
| WO | 2008096143 A1 | 8/2008 |
| WO | 2009/114139 A2 | 9/2009 |
| WO | 2010/017996 | 2/2010 |
| WO | 2011/006073 A1 | 1/2011 |
| WO | 2011/133474 A2 | 10/2011 |
| WO | 2012/030912 A1 | 3/2012 |
| WO | 2012/162394 A2 | 11/2012 |
| WO | 2014/025761 A1 | 2/2014 |
| WO | 2017/024037 A1 | 2/2017 |
| WO | 2018/214980 A1 | 11/2018 |

OTHER PUBLICATIONS

Cole, Bridget M., et al., U.S. Appl. No. 16/815,325, filed Mar. 11, 2019.

Cole, Bridget M., et al., U.S. Appl. No. 16/815,962, filed Mar. 11, 2019.

Cole, Bridget M., et al., U.S. Appl. No. 16/816,018, filed Mar. 11, 2019.

Cole, Bridget M., et al., U.S. Appl. No. 16/676,023, filed Mar. 11, 2019.

Cole, Bridget M., et al., U.S. Appl. No. 16/676,043, filed Mar. 11, 2019.

Ross, S. B., et al., "Cyclization of Three N-ω-Haloalkyl-N-Methylaminoaceto-2,6-Xylidide Derivatives in Relation to Their

(56) References Cited

OTHER PUBLICATIONS

Local Anesthetic Effect in Vitro and in Vivo," J. of Pharm. & Exp. Therapeutics (1972), vol. 182 (2), pp. 351-361.
Zhao, Y., et al., "The Quaternary Lidocaine Derivative QX-314 Produces Long-Lasting Intravenous Regional Anesthesia in Rats," PLoS ONE 9(6): e99704 (2014).
Caplus Accession No. 1975:526218, Abstract of Ross, "Pharmacokinetics of haloalkylamines. Cyclization and distribution in blood in vitro and in vivo," Journal of Pharmacy and Pharmacology, 27(5): 322-8 (1975).
Neilsen, A. B., et al., "Assessment of the combined approach of N-alkylation and salt formation to enhance aqueous solubility of tertiary amines using bupivacaine as a model drug," European Journal of Pharmaceutical Sciences, 24: 85-93 (2005).
Neilsen, A. B., et al., "Bioreversible quaternary N-acyloxymethyl derivatives of the tertiary amines bupivacaine and lidocaine—synthesis, aqueous solubility and stability in buffer, human plasma and simulated intestinal fluid," European Journal of Pharmaceutical Sciences, 24: 433-440 (2005).
Strichartz, G. R., "The Inhibition of Sodium Currents in Myelinated Nerve by Quaternary Derivatives of Lidocaine," The Journal of General Physiology, 62: 37-57 (1973).
Wang, G. K., "Quaternary Ammonium Derivative of Lidocaine as a Long-acting Local Anesthetic," Anesthesiology, 83: 1293-1301 (1995).
Wang, G. K., et al., "N-Butyl Tetracaine as a Neurolytic Agent for Ultralong Sciatic Nerve Block," Anesthesiology, 85: 1386-94 (1996).
Blair, et al., "Quaternary quinidine derivatives as a toll to study: block of human potassium channels," Biophys J., 66(2): A143 (1994).
Cahalan, M. D., et al., "Interactions Between Quaternary Lidocaine, the Sodium Channel Gates, and Tetrodotoxin," Biophys. J., 27: 39-56 (1979).
Huang, L.-Y., M., et al., "Local Anesthetics QX 572 and Benzocaine Act at Separate Sites on the Batrachotoxin-activated Sodium Channel," J. Gen. Physiol. 77: 137-153 (1981).
Binshtok, A. M., et al., "Co-application of Lidocaine and the Permanently Charged Sodium Channel Blocker QX-314 Produces a Long-lasting Nociceptive Blockade in Rodents," Anesthesiology, 111(1): 127-137 (2009).
Longobardo, M., et al., "Effects of a quaternary bupivacaine derivative on delayed rectifer K+ currents," British Journal of Pharmacology, 130: 391-401 (2000).
Machine Translation for CH311608, https://patents.google.com/patent/CH311608A/en?oq=ch311608, 1955.
Caplus Accession No. 1957: 25660 for CH311608, "Basically substituted fatty acid 2-halo-6-methylanilides," Cilag AG, 1956.
Senda, et al., Pharmaceutica Acta Helvetiae, 38: 470-473 (1963).
Nanya, Nihon Yakurigaku Zasshi, "[On the Antispasmodic Action of New Compounds With an Aminoacylamino Side Chain]," 59: 113-122 (1963).
Machine Translation for CH311615, https://patents.google.com/patent/CH311615A/en?oq=ch311615, 1955.
Caplus Accession No. 1957: 25667 for CH311615, "Basically substituted fatty acid 2-halo-6-methylanilides," Cilag AG, 1956.
Machine Translation for CH311614, https://patents.google.com/patent/CH311614A/en?oq=ch311614, 1955.
Caplus Accession No. 1957: 25666 for CH311614, "Basically substituted fatty acid 2-halo-6-methylanilides," Cilag AG, 1956.
Machine Translation for CH311614, https://patents.google.com/patent/CH311613A/en?oq=ch311613, 1955, CH311613.
Caplus Accession No. 1957: 25665 for CH311613, "Basically substituted fatty acid 2-halo-6-methylanilides," Cilag AG, 1956.
Machine Translation for CH311612, https://patents.google.com/patent/CH311612A/en?oq=ch311612, 1955.
Caplus Accession No. 1957: 25664 for CH311612, "Basically substituted fatty acid 2-halo-6-methylanilides," Cilag AG, 1956.
Machine Translation for CH311611, https://patents.google.com/patent/CH311611A/en?oq=ch311611, 1955.
Caplus Accession No. 1957: 25663 for CH311611, "Basically substituted fatty acid 2-halo-6-methylanilides," Cilag AG, 1956.
Caplus Accession No. 1957: 25662 for CH311610, "Basically substituted fatty acid 2-halo-6-methylanilides," Cilag AG, 1956.
Machine Translation for DD298726, https://patents.google.com/patent/DD298726A5/en?oq=dd298726, 1992.
Caplus Accession No. 1992: 485235 for DD298726, "Preparation of morpholinioalkanecarboxylate fungicides," Berlin Bio Zentralanstalt, 1992.
Caplus Accession No. 1957: 25661 for CH311609, "Basically substituted fatty acid 2-halo-6-methylanilides," Cilag AG, 1956.
Caplus Accession No. 1957: 25659 for CH311607, "Basically substituted fatty acid 2-halo-6-methylanilides," Cilag AG, 1956.
Caplus Accession No. 1957: 25658 for CH311606, "Basically substituted fatty acid 2-halo-6-methylanilides," Cilag AG, 1956.
Machine Translation for DD298727, https://patents.google.com/patent/DD298727A5/en?oq=dd298727, 1992.
Caplus Accession No. 1992: 485236 for DD298727, "Preparation of morpholinocarboxylic acid anilide derivatives as microbicides," Berlin Bio Zentralanstalt, 1992.
Machine Translation for DD298723, https://patents.google.com/patent/DD298723A5/en?oq=dd298723, 1992.
Caplus Accession No. 1992: 545294 for DD298723, "Preparation of piperidiniocarboxylic acid anilides as microbicides," Berlin Bio Zentralanstalt, 1992.
Caplus Accession No. 1960:50209, Abstract of Kudryashova et al., "Arylamides of dialkylaminoacetic acids," Zhurnal Obshchei Khimii, 29: 1240-4, 1959.
Caplus Accession No. 1960:118311, Abstract of Nikitskaya et al., "Bicyclic systems based on 2,6-lutidine. III. N-Derivatives of 3,9-oxazabicyclo[3.3.1]nonane," Zhurnal Obshchei Khimii, 30: 171-82 (1960).
Caplus Accession No. 1965:488540, Abstract of Dahlbom et al., "Quaternary derivatives of aminoacylanilines. II. N,N-Bis(arylcarbamoylalkyl)ammonium salts, a class of new compounds with antiarrhythmic activity," Acta Pharm. Suecica, 2(3): 219-26 (1965).
Caplus Accession No. 1968:12899, Abstract of Kornet, "Synthesis of 1-methylpyrazolidine and some of its derivatives," Journal of Pharmaceutical Sciences, 56(8): 963-6 (1967).
Caplus Accession No. 1971:86121, Abstract of Ross et al., "Formation of a quaternary derivative in mouse brain after administration of N-(5'-chloropentyl)-N-methylaminoaceto-2,6-xylidide," European Journal of Pharmacology, 13(1): 46-50 (1970).
Caplus Accession No. 1971:418154, Abstract of Ross et al., "Formation of a piperidinium derivative from N-(5'-chloropentyl)-N-methylaminoaceto-2,6-xylidide in relation to the sustained local anesthetic action on the sciatic nerve of the guinea pig in vivo," Nature (London), New Biology, 230(17): 274-5 (1971).
Caplus Accession No. 1972:496963, Abstract of Ross et al., "Cyclization of three N-ω-haloalkyl-N-methylaminoaceto-2,6-xylidide derivatives in relation to their local anesthetic effect in vitro and in vivo," Journal of Pharmacology and Experimental Therapeutics, 182(2): 351-61 (1972).
PubChem, SID: 104085346, Jan. 20, 2011.
Georgescu, E. et al., "New N-bridgehead heterocyclic compounds. I. Carbamoyl-substituted indolizines and benzoindolizines", ARKIVOC 2002, vol. 2, Gainsesville, FL, United States [online computer file], http://www.arkat-usa.org/ark/ujournal/2002/Nenitzescu/CN-%20290/CN-290.pdf, 2002, 30-45.

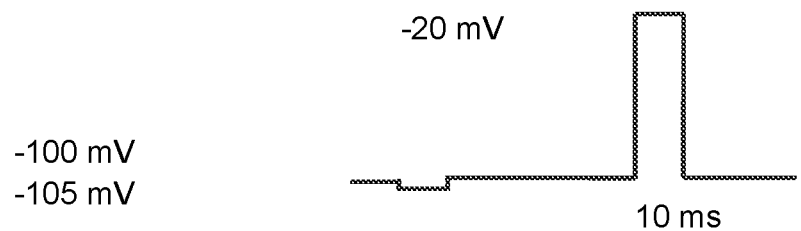

CHARGED ION CHANNEL BLOCKERS AND METHODS FOR USE

RELATED APPLICATION

This application claims the benefit of U.S. Provisional Application Ser. No. 62/816,434 filed Mar. 11, 2019. The entire contents of the above application are incorporated by reference herein.

TECHNICAL FIELD

The present invention relates generally to quaternary ammonium compounds, pharmaceutical compositions, and methods useful as selective inhibitors of pain, cough and itch sensing neurons (nociceptors, cough receptors and pruriceptors) and in the treatment of neurogenic inflammation.

BACKGROUND OF THE INVENTION

The invention features compounds, compositions and methods for the selective inhibition of sensory neurons (nociceptors, cough receptors and pruriceptors) and the treatment of neurogenic inflammation by targeting nociceptors with a small molecule drug, while minimizing effects on non-nociceptive neurons or other types of cells. According to the method of the invention, small, cationic drug molecules gain access to the intracellular compartment of sensory neurons via entry through large pore receptor/ion channels that are present in pain-coughand itch-sensing neurons but to a lesser extent or not at all in other types of neurons or in other types of tissue.

Local anesthetics such as lidocaine and articaine act by inhibiting voltage-dependent sodium channels in neurons. These anesthetics block sodium channels and thereby the excitability of all neurons, not just pain-sensing neurons (nociceptors). Thus, while the goal of topical or regional anesthesia is to block transmission of signals in nociceptors to prevent pain, administration of local anesthetics also produces unwanted or deleterious effects such as general numbness from block of low threshold pressure and touch receptors, motor deficits and/or paralysis from block of motor axons and other complications from block of autonomic fibers. Local anesthetics are relatively hydrophobic molecules that gain access to their blocking site on the sodium channel by diffusing through the cell membrane. Charged derivatives of these compounds, which are not membrane-permeable, have no effect on neuronal sodium channels when applied to the external surface of the nerve membrane but can block sodium channels if somehow introduced inside the cell, for example by diffusion from a micropipette used for whole-cell electrophysiological recording from isolated neurons. Pain-, cough-, and itch-sensing neurons differ from other types of neurons in expressing (in most cases) the TRPV1 receptor/channel, which is activated by painful heat or by capsaicin, the pungent ingredient in chili pepper. Other types of channels selectively expressed in various types of pain-sensing, cough-sensing and itch-sensing (pruriceptor) neurons include but are not limited to TRPV2-4, TRPA1, TRPM8, ASIC and P2X(2/3) channels. It is well established that some cationic small molecules such as QX-314 are able to enter a cell via passage through activated large pore channels such as TRPV1.

Neuropathic, inflammatory, and nociceptive pain differ in their etiology, pathophysiology, diagnosis, and treatment. Nociceptive pain occurs in response to the activation of a specific subset of high threshold peripheral sensory neurons, the nociceptors, by intense or noxious stimuli. It is generally acute, self-limiting and serves a protective biological function by acting as a warning of potential or on-going tissue damage. It is typically well-localized. Examples of nociceptive pain include, but are not limited to, traumatic or surgical pain, labor pain, sprains, bone fractures, burns, bumps, bruises, injections, dental procedures, skin biopsies, and obstructions.

Inflammatory pain is pain that occurs in the presence of tissue damage or inflammation including postoperative (i.e. pain associated with acute perioperative pain resulting from inflammation caused by tissue trauma (e.g., surgical incision, dissection, burns) or direct nerve injury (e.g., nerve transection, stretching, or compression)), post-traumatic pain, arthritic pain (rheumatoid; or osteoarthritis (i.e. joint pain and stiffness due to gradual deterioration of the joint cartilage; risk factors include aging, injury, and obesity; commonly affected joints are the hand, wrist, neck, knee, hip, and spine), pain and pain associated with damage to joints, muscle, and tendons as in axial low back pain (i.e. a prevalent, painful condition affecting the lower portion of the back; common causes include muscle strain, spine fracture, bulging or ruptured disc, and arthritis), severe nociceptive pain may transition to inflammatory pain if there is associated tissue injury.

Neuropathic pain is a common type of chronic, non-malignant pain, which is the result of an injury or malfunction in the peripheral or central nervous system and serves no protective biological function. It is estimated to affect more than 1.6 million people in the U.S. population. Neuropathic pain has many different etiologies, and may occur, for example, due to trauma, surgery, herniation of an intervertebral disk, spinal cord injury, diabetes, infection with herpes zoster (shingles), HIV/AIDS, late-stage cancer, amputation (including mastectomy), carpal tunnel syndrome, chronic alcohol use, exposure to radiation, and as an unintended side-effect of neurotoxic treatment agents, such as certain anti-HIV and chemotherapeutic drugs. Peripheral neuropathy is caused by damages to the peripheral nerves from injury, trauma, prolonged pressure, or inflammation causing numbness and pain in corresponding areas of the body.

Neuropathic pain is frequently described as "burning," "electric," "tingling," or "shooting" in nature. It is often characterized by chronic dynamic allodynia (defined as pain resulting from a moving stimulus that does not ordinarily elicit a painful response, such as light touch) and hyperalgesia (defined as an increased sensitivity to a normally painful stimulus) and may persist for months or years beyond the apparent healing of any damaged tissues.

Pain may occur in patients with cancer, which may be due to multiple causes; inflammation, compression, invasion, metastatic spread into bone or other tissues.

There are some conditions where pain occurs in the absence of a noxious stimulus, tissue damage or a lesion to the nervous system, called dysfunctional pain and these include but are not limited to fibromyalgia, tension type headache, and irritable bowel disorders.

Migraine is a headache associated with the activation of sensory fibers innervating the meninges of the brain.

Itch (pruritus) is a dermatological condition that may be localized and generalized and can be associated with skin lesions (rash, atopic eczema, wheals). Itch accompanies many conditions including but not limited to stress, anxiety, UV radiation from the sun, metabolic and endocrine disorders (e.g., liver or kidney disease, hyperthyroidism), cancers (e.g., lymphoma), reactions to drugs or food, parasitic and fungal infections, allergic reactions, diseases of the blood (e.g., polycythemia vera), and dermatological conditions. Itch is mediated by a subset of small diameter primary sensory neurons, the pruriceptor, that share many features of nociceptor neurons, including but not limited to expression of TRPV1 channels and other large pore channels (e.g. TRPV2-4, TRPA1, TRPM8, ASIC and P2X(2/3). Certain itch mediators-such as eicosanoids, histamine, bradykinin, ATP, and various neurotrophins have endovanilloid functions. Topical capsaicin suppresses histamine-induced itch. Pruriceptors like nociceptors are therefore a suitable target for this method of delivering ion channel blockers.

Cough is a defensive reflex designed to protect the airway from foreign bodies and to aid in the clearance of luminal debris. This reflex, however, can became aberrant in a number of diseases leading to a non-productive dry cough where hyper- or allo-tussive states exist. Hyper- and allo-tussive states are often chronic in nature lasting greater than three months and can be manifested in many airway diseases states including asthma, COPD, asthma-COPD overlap syndrome (ACOS), interstitial pulmonary fibrosis (IPF) and lung cancer. In addition, inappropriate cough reflexes can be manifested acutely and chronically following viral infection. Furthermore, chronic cough can be idiopathic in nature with unknown etiology.

Neurogenic inflammation is a mode of inflammation mediated by the efferent (motor) functions of sensory neurons, in which pro-inflammatory mediator molecules released in the periphery by pain-sensing neurons (nociceptors) both activate a variety of inflammatory pathways in immune cells, and also act on the vascular system to alter blood flow and capillary permeability.

Neurogenic inflammation contributes to the peripheral inflammation elicited by tissue injury, autoimmune disease, infection, allergy, exposure to irritants in a variety of tissues, and is thought to play an important role in the pathogenesis of numerous disorders (e.g. migraine, arthritis, rhinitis, gastritis, colitis, cystitis, and sunburn). One way to reduce neurogenic inflammation is to block excitability in nociceptors, thereby preventing the activation of nociceptor peripheral terminals and the release of pro-inflammatory chemicals.

Despite the development of a variety of therapies for pain, itch, and neurogenic inflammation, there is a need for additional agents.

SUMMARY OF THE INVENTION

The present invention provides compounds represented by Formula (I) that can be used to treat or prevent pain, itch, cough, and neurogenic inflammation:

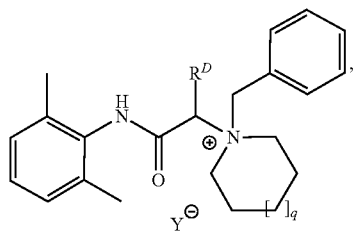

(I)

wherein:

$Y^-$ is a pharmaceutically acceptable anion;

q is 0, 1, 2, or 3; and $R^D$ is hydrogen, methyl, or ethyl.

BRIEF DESCRIPTION OF THE DRAWING

The FIGURE illustrates the voltage protocol used in the Whole Cell Patch Clamp Protocol.

DETAILED DESCRIPTION OF THE INVENTION

The present invention provides compounds represented by Formula (I) as described above, or pharmaceutically acceptable salts, stereoisomers, solvates, hydrates or combinations thereof. The invention also provides compositions comprising compounds having Formula (I) or a pharmaceutically acceptable salts thereof, for example, a composition comprising an effective amount of a compound of Formula (I) or a pharmaceutically acceptable salt thereof, and a pharmaceutically acceptable excipient. The compositions of the invention may further comprise compounds of the invention and a biologically active agent. The compositions can be formulated for oral, intravenous, intramuscular, rectal, cutaneous, subcutaneous, topical, transdermal, sublingual, nasal, inhalation, vaginal, intrathecal, epidural, or ocular administration.

The invention further provides methods for treating pain, itch, cough, or a neurogenic inflammatory disorder in a patient, including administering to the patient a composition comprising a compound having Formula (I), wherein the compound inhibits one or more voltage-gated ion channels present in nociceptors and/or cough receptors and/or pruriceptors when exposed or applied to the internal face of the channels but does not substantially inhibit the channels when applied to the external face of the channels, and wherein the compound is capable of entering nociceptors, cough receptors or pruriceptors through a large pore channel when the channel is activated and inhibiting one or more voltage-gated ion channels present in the nociceptors cough receptors or pruriceptors.

In certain embodiments, the large pore channel is a transient receptor potential ion channel (TRP channel). In other embodiments, the TRP channel is activated by an exogenous or endogenous agonist. In yet other embodiments, the large pore channel is TRPA1, TRPV1-4, TRPM8, ASIC or P2X. In particular embodiments, the compound is capable of entering nociceptors, cough receptors or pruriceptors through the TRPA1 TRPV1-4, TRPM8, ASIC or P2X receptor/channel when the receptor/channel is activated. In yet other embodiments, the compound inhibits voltage-gated sodium channels. In yet another embodiment, the type of pain treated by the methods, compositions, and kits of the invention is selected from the group consisting of neuropathic pain, inflammatory pain, nociceptive pain, pain due to infections, and procedural pain, or wherein the neurogenic inflammatory disorder is selected from the group consisting of allergic inflammation, asthma, chronic cough, conjunctivitis, rhinitis, psoriasis, inflammatory bowel disease, interstitial cystitis, and atopic dermatitis.

We have identified compounds having Formula (I)

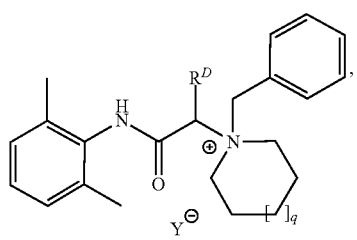

that are capable of passing through open large pore channels that are expressed on nociceptors and/or cough receptors and/or pruriceptors but not on motor neurons. Because the ion channel blocking compounds of the present invention are positively charged, they are not membrane-permeable and thus cannot enter cells that do not express large pore channels. Since large pore channels are often more active in tissue conditions associated with pain (such as inflammation) due to release of endogenous ligands or activation by thermal stimuli, the ion channel blocker of the invention can be used alone to selectively target activated nociceptors in order to effectively treat (e.g., eliminate or alleviate) pain, cough, itch, or neurogenic inflammation. The ion channel blockers of the invention can also be used in combination with one or more exogenous large pore channel agonists to selectively target nociceptors in order to effectively treat (e.g., eliminate or alleviate) pain, itch, or neurogenic inflammation.

Voltage-dependent ion channels in pain-sensing neurons are currently of great interest in developing drugs to treat pain. Blocking voltage-dependent sodium channels in pain-sensing neurons can block pain signals by interrupting initiation and transmission of the action potential. Moreover, blocking voltage-dependent sodium channels in nociceptors can reduce or eliminate neurogenic inflammation by preventing activation of nociceptor peripheral terminals and the release thereof pro-inflammatory chemicals.

Heretofore, a limitation in treating with molecules that block sodium channels or calcium channels is that the vast majority of such externally-applied molecules are hydrophobic and can pass through membranes. Because of this, they will enter all cells and thus have no selectivity for affecting only nociceptors.

The inhibitors of the present invention are membrane-impermeable and are only effective when present inside the nociceptor cell, and thus must pass through the cell membrane via a channel or receptor, such as large pore channels (e.g., TRPAV1-4, TRPA1, TRPM8, ASIC and P2X(2/3)), in order to produce an effect. Under normal circumstances, most large pore channels in nociceptors are not active but require a noxious thermal, mechanical, or chemical stimulus to activate them. For example, TRP channels in nociceptors can be activated by an exogenous TRP ligand (i.e. TRP agonist) such as capsaicin, which opens the TRPV1 channel. Thus, one approach to selectively targeting nociceptors is to co-administer the membrane-impermeable ion channel inhibitor with an exogenous TRP ligand that permits passage of the inhibitor through the TRP channel into the cell. In addition to capsaicin, the exogenous TRP ligand can also be another capsaicinoid, mustard oil, or lidocaine. In another example, TRP channels may be active in response to exogenous irritant activators such as inhaled acrolein from smoke or chemical warfare agents such as tear gas.

Under certain circumstances, large pore channels can be activated in the absence of exogenous large pore channel agonists/ligands by endogenous inflammatory activators that are generated by tissue damage, infection, autoimmunity, atopy, ischemia, hypoxia, cellular stress, immune cell activation, immune mediator production, and oxidative stress. Under such conditions, endogenous molecules (e.g., protons, lipids, and reactive oxygen species) can activate large pore channels expressed on nociceptors, allowing membrane-impermeable, voltage-gated ion channel blockers to gain access to the inside of the nociceptor through the endogenously-activated large pore channels. Endogenous inflammatory activators of large pore channels include, for example, prostaglandins, nitric oxide (NO), peroxide ($H_2O_2$), cysteine-reactive inflammatory mediators like 4-hydroxynonenal, endogenous alkenyl aldehydes, endocannabinoids, and immune mediators (e.g., interleukin 1 (IL-1), nerve growth factor (NGF), and bradykinin, whose receptors are coupled to large pore channels).

Definitions

As used herein, the words "a" and "an" are meant to include one or more unless otherwise specified.

By "biologically active" is meant that a molecule, including biological molecules, such as nucleic acids, peptides, polypeptides, and proteins, exerts a biological, physical or chemical effect activity on a protein, enzyme, receptor, ligand, antigen, itself or other molecule. For example, a "biologically active" molecule may possess, e.g., enzymatic activity, protein binding activity, or pharmacological activities.

Biologically active agents that can be used in the methods and kits described herein include, without limitation, TRP1A receptor agonists, TRPV1-4 receptor agonists, ASIC agonists, TRPM8 agonists, P2X receptor agonists, NSAIDs, glucocorticoids, narcotics, anti-proliferative and immune modulatory agents, an antibody or antibody fragment, an antibiotic, a polynucleotide, a polypeptide, a protein, an anti-cancer agent, a growth factor, and a vaccine.

By "inflammation" is meant any types of inflammation, such those caused by the immune system (immune-mediated inflammation) and by the nervous system (neurogenic inflammation), and any symptom of inflammation, including redness, heat, swelling, pain, and/or loss of function.

By "neurogenic inflammation" is meant any type of inflammation mediated or contributed to by neurons (e.g. nociceptors) or any other component of the central or peripheral nervous system.

The term "pain" is used herein in the broadest sense and refers to all types of pain, including acute and chronic pain, such as nociceptive pain, e.g. somatic pain and visceral pain; inflammatory pain, dysfunctional pain, idiopathic pain, neuropathic pain, e.g., centrally generated pain and peripherally generated pain, migraine, and cancer pain.

The term "nociceptive pain" is used to include all pain caused by noxious stimuli that threaten to or actually injure body tissues, including, without limitation, by a cut, bruise, bone fracture, crush injury, burn, and the like. Pain receptors for tissue injury (nociceptors) are located mostly in the skin, musculoskeletal system, or internal organs.

The term "somatic pain" is used to refer to pain arising from bone, joint, muscle, skin, or connective tissue. This type of pain is typically well localized.

The term "visceral pain" is used herein to refer to pain arising from visceral organs, such as the respiratory, gastrointestinal tract and pancreas, the urinary tract and reproductive organs. Visceral pain includes pain caused by tumor involvement of the organ capsule. Another type of visceral pain, which is typically caused by obstruction of hollow viscus, is characterized by intermittent cramping and poorly localized pain. Visceral pain may be associated with inflammation as in cystitis or reflux esophagitis.

The term "inflammatory pain" includes pain associates with active inflammation that may be caused by trauma, surgery, infection and autoimmune diseases.

The term "neuropathic pain" is used herein to refer to pain originating from abnormal processing of sensory input by the peripheral or central nervous system consequent on a lesion to these systems.

The term "procedural pain" refers to pain arising from a medical, dental or surgical procedure wherein the procedure is usually planned or associated with acute trauma.

The term "itch" is used herein in the broadest sense and refers to all types of itching and stinging sensations localized and generalized, acute intermittent and persistent. The itch may be idiopathic, allergic, metabolic, infectious, drug-induced, due to liver, kidney disease, or cancer. "Pruritus" is severe itching.

By "patient" is meant any animal. In one embodiment, the patient is a human. Other animals that can be treated using the methods, compositions, and kits of the invention include but are not limited to non-human primates (e.g., monkeys, gorillas, chimpanzees), domesticated animals (e.g., horses, pigs, goats, rabbits, sheep, cattle, llamas), and companion animals (e.g., guinea pigs, rats, mice, lizards, snakes, dogs, cats, fish, hamsters, and birds).

Compounds useful in the invention include, but are not limited to, those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein. The term "pharmaceutically acceptable anion" as used herein, refers to the conjugate base of a pharmaceutically acceptable acid. Such acids are described in Stahl, P. H. and Wermuth, C. G. (eds.), Handbook of Pharmaceutical Salts: Properties, Selection and Use, Wiley VCH (2008). Pharmaceutically acceptable acids include, but are not limited to, acetic acid, dichloroacetic acid, adipic acid, alginic acid, L-ascorbic acid, L-aspartic acid, benzenesulfonic acid, 4-acetamidobenzoic acid, benzoic acid, p-bromophenylsulfonic acid, (+)-camphoric acid, (+)-camphor-10-sulfonic acid, capric acid, caproic acid, caprylic acid, carbonic acid, cinnamic acid, cyclamic acid, dodecylsulfuric acid, ethane-1,2-disulfonic acid, ethanesulfonic acid, 2-hydroxyethanesulfonic acid, sulfuric acid, boric acid, citric acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycolic acid, hippuric acid, hydrochloric acid, hydrobromic acid, hydroiodic acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, oleic acid, orotic acid, oxalic acid, palmitic acid, pamoic acid, phosphoric acid, propionic acid, (−)-L-pyroglutamic acid, salicyclic acid, 4-aminosalicyclic acid, sebacic acid, stearic acid, succinic acid, (+)-L-tartaric acid, thiocyanic acid, p-toluenesulfonic acid, and undecylenic acid. Pharmaceutically acceptable anions include the conjugate base of any the acids set forth above.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. The salts can be prepared in situ during the final isolation and purification of the compounds of the invention, or separately by reacting the free base function with a suitable organic acid. Representative acid addition salts include but are not limited to acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

By "charged moiety" is meant a moiety which gains a proton at physiological pH thereby becoming positively charged (e.g., ammonium, guanidinium, or amidinium) or a moiety that includes a net formal positive charge without protonation (e.g., quaternary ammonium). The charged moiety may be either permanently charged or transiently charged.

By "therapeutically effective amount" or "effective amount" means an amount sufficient to produce a desired result, for example, the reduction or elimination of pain, cough, itch, or neurogenic inflammation in a patient (e.g., a human) suffering from a condition, disease, or illness that is caused wholly or in part by neurogenic inflammation (e.g. asthma, arthritis, colitis, contact dermatitis, diabetes, eczema, cystitis, chronic refractory cough, post-viral cough, gastritis, migraine headache, psoriasis, rhinitis, rosacea, or sunburn).

"Solvates" means solvent addition forms that contain either stoichiometric or nonstoichiometric amounts of solvent.

The compounds of the present invention, including salts of the compounds, can exist in unsolvated forms as well as solvated forms, including hydrated forms and unhydrated forms. In general, the solvated forms are equivalent to unsolvated forms and are encompassed within the scope of the present invention. Nonlimiting examples of hydrates include monohydrates, dihydrates, hemihydrates, etc. In certain aspects, the compound is a hemihydrate. Nonlimiting examples of solvates include ethanol solvates, acetone solvates, etc.

The compounds of the invention may exist in multiple crystalline or amorphous forms. In general, all physical forms are equivalent for uses contemplated by the present invention and are intended to be within the scope of the invention.

Compounds that can be used in the compositions, kits, and methods of the invention include compounds having Formula (I), or a pharmaceutically acceptable salt thereof:

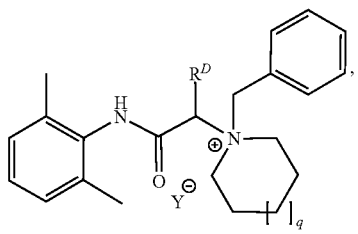
(I)

wherein Y⁻, q and $R^D$ are as defined herein.

In some embodiments Y⁻ is a halide anion, a carboxylate, or a sulfonate. Y⁻ can, for example, be a halide ion, a substituted or unsubstituted alkylsulfonate, a substituted or unsubstituted arylsulfonate, a substituted or unsubstitued alkyl or aliphatic carboxylate, a substituted or unsubstituted aryl carboxylate, or a substituted or unsubstituted heterocyclyl carboxylate.

In certain embodiments, Y⁻ is selected from the group consisting of trifluoroacetate, sulfate, phosphate, acetate, fumarate, formate, carbonate, maleate, citrate, pyruvate, succinate, oxalate, a sulfonate, (for example, methanesulfonate, trifluoromethanesulfonate, toluenesulfonate such as p-toluenesulfonate, benzenesulfonate, ethanesulfonate, camphorsulfonate, 2-mesitylenesulfonate, or naphthalenesulfonate such as 2-naphthalenesulfonate), bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), D-mandelate, L-mandelate, propionate, tartarate, phthalate, hydrochlorate, hydrobromate, and nitrate.

In one embodiment, Y⁻ is halide anion. In a preferred embodiment, Y⁻ is selected from the halide ions bromide, chloride, or iodide.

As will be understood, when q is 0, 1, 2, or 3, the N⁺-containing ring of Formula (I) is:

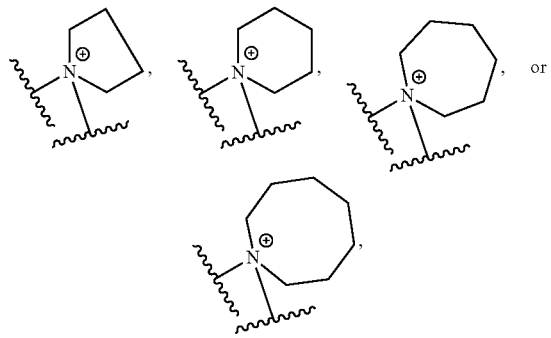

respectively. In certain preferred embodiments, q is 0. In other preferred aspects, q is 1. In yet further preferred aspects, q is 2. In additional aspects, q is 3.

In yet additional preferred aspects, $R^D$ is hydrogen.
In further aspects, $R^D$ is methyl.
In yet other aspects, $R^D$ is ethyl.
In yet further preferred aspects, q is 0 and $R^D$ is hydrogen.
In additional preferred aspects, q is 1 and $R^D$ is hydrogen.
In further preferred aspects, q is 2 and $R^D$ is hydrogen.
In additional preferred aspects, q is 3 and $R^D$ is hydrogen.
In yet additional preferred embodiments, q is 0 and $R^D$ is methyl.
In additional preferred aspects, q is 1 and $R^D$ is methyl.
In further preferred aspects, q is 2 and $R^D$ is methyl.
In additional preferred aspects, q is 3 and $R^D$ is methyl.
In further preferred embodiments, q is 0 and $R^D$ is ethyl.
In additional preferred aspects, q is 1 and $R^D$ is ethyl.
In further preferred aspects, q is 2 and $R^D$ is ethyl.
In additional preferred aspects, q is 3 and $R^D$ is ethyl.

Each preferred group stated above can be taken in combination with one, any or all other preferred groups.

In additional preferred aspects, the compound is selected from Table A below, wherein Y⁻ is a pharmaceutically acceptable anion:

| Compound No. | Structure |
|---|---|
| 1' | 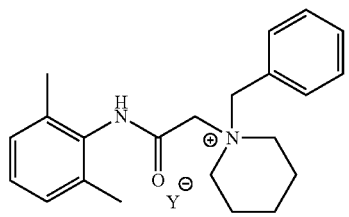 |
| 2' | 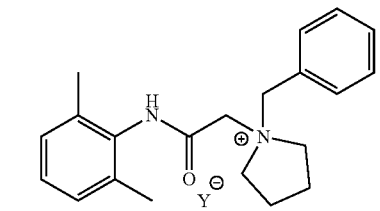 |
| 3' | 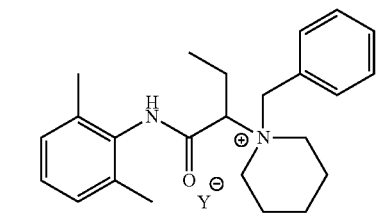 |
| 4' | 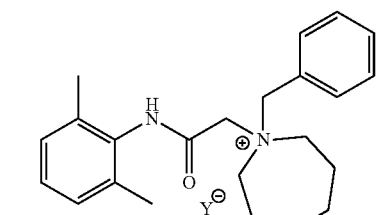 |
| 5' | 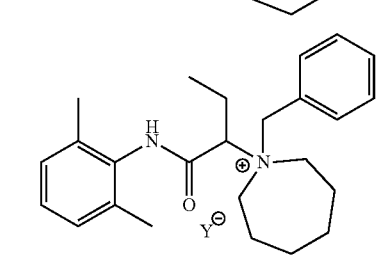 |

-continued

| Compound No. | Structure |
|---|---|
| 6' | [structure: 2,6-dimethylphenyl-NH-C(=O)-CH2-N⁺(azocane), Y⁻] |

In further preferred aspects, the compound is selected from Table B below:

TABLE B

| Compound # | Structure |
|---|---|
| 1'A | [structure: 2,6-dimethylphenyl-NH-C(=O)-CH2-N⁺(piperidine)(benzyl), Br⁻] |
| 1'B | [structure: 2,6-dimethylphenyl-NH-C(=O)-CH2-N⁺(piperidine)(benzyl), Cl⁻] |
| 2'A | [structure: 2,6-dimethylphenyl-NH-C(=O)-CH2-N⁺(pyrrolidine)(benzyl), Br⁻] |
| 2'B | [structure: 2,6-dimethylphenyl-NH-C(=O)-CH2-N⁺(pyrrolidine)(benzyl), Cl⁻] |
| 3'A | [structure: 2,6-dimethylphenyl-NH-C(=O)-CH(Et)-N⁺(piperidine)(benzyl), Br⁻] |
| 3'B | [structure: 2,6-dimethylphenyl-NH-C(=O)-CH(Et)-N⁺(piperidine)(benzyl), Cl⁻] |
| 4'A | [structure: 2,6-dimethylphenyl-NH-C(=O)-CH2-N⁺(azocane)(benzyl), Br⁻] |
| 4'B | [structure: 2,6-dimethylphenyl-NH-C(=O)-CH2-N⁺(azocane)(benzyl), Cl⁻] |
| 5'A | [structure: 2,6-dimethylphenyl-NH-C(=O)-CH(Et)-N⁺(azocane)(benzyl), Br⁻] |
| 5'B | [structure: 2,6-dimethylphenyl-NH-C(=O)-CH(Et)-N⁺(azocane)(benzyl), Cl⁻] |
| 6'A | [structure: 2,6-dimethylphenyl-NH-C(=O)-CH2-N⁺(azocane larger ring)(benzyl), Br⁻] |
| 6'B | [structure: 2,6-dimethylphenyl-NH-C(=O)-CH2-N⁺(azocane larger ring)(benzyl), Cl⁻] |

Each preferred embodiment described herein can be taken in combination with one, any or all other preferred embodiments, as though presented herein in every permutation.

Compositions of the invention can comprise racemic mixtures, pure enantiomers, or an excess of one enantiomer over the other. For example, a composition can comprise an enantiomeric excess of at least 5, 10, 20, 30, 40, 50, 60, 70, 80 or 90%. In one embodiment, the enantiomeric excess is at least 95%.

The compounds of the invention include all enantiomers which may be defined, in terms of absolute stereochemistry, as (R)- or (S)-, as well as their racemic and optically pure forms, and is not limited to those described herein in any of their pharmaceutically acceptable forms, including enantiomers, salts, solvates, polymorphs, solvatomorphs, hydrates, anhydrous and other crystalline forms and combinations thereof. Likewise, all tautomeric forms are intended to be included.

Preferably, a pharmaceutical composition comprises a compound of the invention as an R enantiomer in substantially pure form; or, a pharmaceutical composition comprises a compound of the invention as an S enantiomer in substantially pure form; or, a pharmaceutical composition comprises a compound of the invention as enantiomeric mixtures which contain an excess of the R enantiomer or an excess of the S enantiomer. It is particularly preferred that the pharmaceutical composition contains a compound of the invention which is a substantially pure optical isomer. For the avoidance of doubt, a compound of the invention can, if desired, be used in the form of solvates.

Compounds having Formula (I) can be prepared using methods analogous to that described in the Examples and the following synthetic schemes:

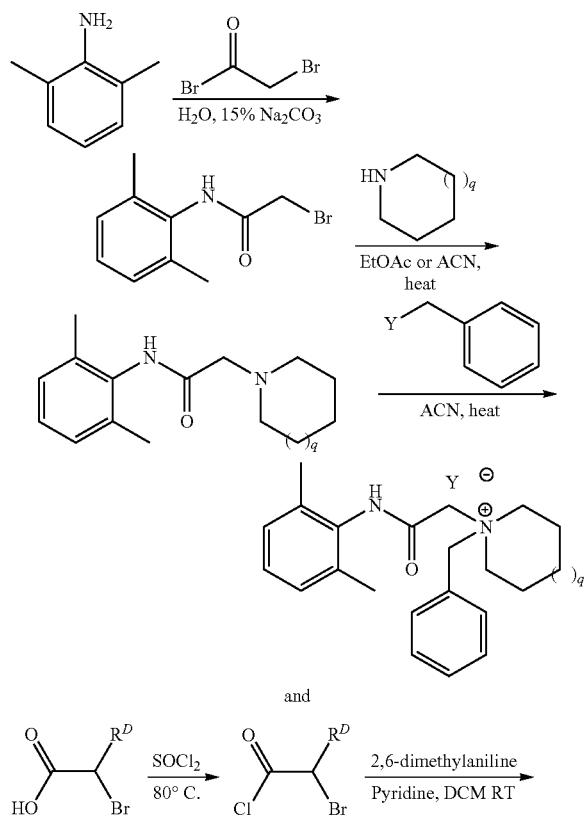

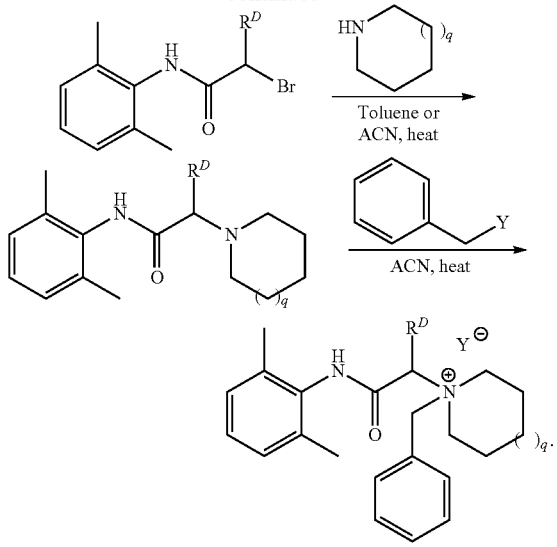

Additional Biologically Active Agents and Exogenous Large Pore Channel Agonists

As described above, the compound or composition of the invention can be administered with a biologically active agent. For example, one or more additional biologically active agents, including those typically used to treat neurogenic inflammation, may be used in combination with a compound or composition of the invention described herein. The biologically active agents include, but are not limited to, TRP1A receptor agonists, TRPV1-4 receptor agonists, TRPM8 agonists, ASIC agonists, P2X receptor agonists, acetaminophen, NSAIDs, glucocorticoids, narcotics, tricyclic antidepressants, amine transporter inhibitors, anticonvulsants, anti-proliferative and immune modulatory agents, an antibody or antibody fragment, an antibiotic, a polynucleotide, a polypeptide, a protein, an anti-cancer agent, a growth factor, and a vaccine.

TRPV1 agonists that can be employed in the methods, kits and compositions of the invention include, but are not limited to, any that activates TRPV1 receptors on nociceptors and allows for entry of at least one inhibitor of voltage-gated ion channels (for example, a compound of the invention). A suitable TRPV1 agonist is capsaicin or another capsaicinoids, which are members of the vanilloid family of molecules. Naturally occurring capsaicinoids are capsaicin itself, dihydrocapsaicin, nordihydrocapsaicin, homodihydrocapsaicin, homocapsaicin, and nonivamide. Other suitable capsaicinoids and capsaicinoid analogs and derivatives for use in the compositions and methods of the present invention include naturally occurring and synthetic capsaicin derivatives and analogs including, e.g., vanilloids (e.g., N-vanillyl-alkanedienamides, N-vanillyl-alkanedienyls, and N-vanillyl-cis-monounsaturated alkenamides), capsiate, dihydrocapsiate, nordihydrocapsiate and other capsinoids, capsiconiate, dihydrocapsiconiate and other coniferyl esters, capsiconinoid, resiniferatoxin, tinyatoxin, civamide, N-phenylmethylalkenamide capsaicin derivatives, olvanil, N-[(4-(2-aminoethoxy)-3-methoxyphenyl)methyl]-9Z-octa-decanamide, N-oleyl-homovanillamide, triprenyl phenols (e.g., scutigeral), gingerols, piperines, shogaols, guaiacol, eugenol, zingerone, nuvanil, NE-19550, NE-21610, and NE-28345. Additional capsaicinoids, their structures, and methods of their manufacture are described in U.S. Pat. Nos. 7,446,226 and 7,429,673, which are hereby incorporated by reference.

Additional suitable TRPV1 agonists include but are not limited to eugenol, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C18 N-acylethanolamines, lipoxygenase derivatives such as 12-hydroperoxyeicosatetraenoic acid, inhibitor cysteine knot (ICK) peptides (vanillotoxins), piperine, MSK195 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-alpha-sanshool, 2-aminoethoxydiphenyl borate, 10-shogaol, oleylgingerol, oleylshogaol, and SU200 (N-(4-tert-butylbenzyl)-N'-(4-hydroxy-3-methoxybenzyl)thiourea). Still other TRPV1 agonists include amylocaine, articaine, benzocaine, bupivacaine, carbocaine, carticaine, chloroprocaine, cyclomethycaine, dibucaine (cinchocaine), dimethocaine (larocaine), etidocaine, hexylcaine, levobupivacaine, lidocaine, mepivacaine, meprylcaine (oracaine), metabutoxycaine, piperocaine, prilocaine, procaine (novacaine), proparacaine, propoxycaine, risocaine, ropivacaine, tetracaine (amethocaine), and trimecaine.

Suitable TRPV2-4 agonists include, but are not limited to, are 2-APB, cannabinol, diphenylboronic anhydride, insulin-like growth factor 1, lysophosphatidylcholine, lysophosphatidylinositol, probenecid, Δ9-tetrahydrocannabinol, vanillin, eugenol, cinnamaldehyde, camphor, carvacrol, thymol, citral, farnesyl diphosphate, tetrahydrocannabivarin, incensole acetate, diphenylboronic anhydride, 6-tert-butyl-m-cresol, dihydrocarveocarveol, borneol, (−)-menthol, GSK1016790A, 4α-PDH, 5,6-epoxyeicosatrienoic acid, 4α-PDD, bisandrographolide, citric acid, phorbol 12-myristate 13-acetate and RN1747.

Suitable TRPM8 agonists include, but are not limited to, are menthol, icilin, eucalyptus, linalool, geraniol, hydroxycitronellal, WS-3, WS-23, Frescolat MGA, Frescolat ML, PMD 38, CPS125, Coolact P, M8-Ag, AITC, cryosim-3 and Cooling Agent 10.

Suitable ASIC agonists include, but are not limited to, chlorophenylguanidine hydrochloride, GMQ hydrochloride, tetrahydropapaveroline (THP), reticulin, polyamine agmatine, lysophosphatidylcholine, arachidonic acid and neuropeptide SF.

Other biologically active agents which can be employed in the methods, compositions, and kits of the invention include any that activates TRP1A receptors on nociceptors or pruriceptors and allows for entry of at least one inhibitor of voltage-gated ion channels. Suitable TRP1A agonists include but are not limited to cinnamaldehyde, allyl-isothiocynanate (mustard oil), diallyl disulfide, icilin, cinnamon oil, wintergreen oil, clove oil, acrolein, hydroxy-alpha-sanshool, 2-aminoethoxydiphenyl borate, 4-hydroxynonenal, methyl p-hydroxybenzoate, and 3'-carbamoylbiphenyl-3-yl cyclohexylcarbamate (URB597).

P2X agonists that can be employed in the methods, compositions, and kits of the invention include any that activates P2X receptors on nociceptors or pruriceptors and allows for entry of at least one inhibitor of voltage-gated ion channels. Suitable P2X agonists include but are not limited to ATP, α,β-methylene ATP, 2-methylthio-ATP, 2' and 3'-O-(4-benzoylbenzoyl)-ATP, and ATP5'-O-(3-thiotriphosphate).

Other biologically active agents that can be used in combination with the compounds of the invention include NSAIDs, glucocorticoids, narcotics, tricyclic antidepressants, amine transporter inhibitors, anticonvulsants, antiproliferative and immune modulatory agents, an antibody or antibody fragment, an antibiotic, a polynucleotide, a polypeptide, a protein, an anti-cancer agent, a growth factor, and a vaccine.

Non-steroidal anti-inflammatory drugs (NSAIDs) that can be administered to a patient (e.g., a human) suffering from neurogenic inflammation in combination with a composition of the invention include, but are not limited to, acetylsalicylic acid, amoxiprin, benorylate, benorilate, choline magnesium salicylate, diflunisal, ethenzamide, faislamine, methyl salicylate, magnesium salicylate, salicyl salicylate, salicylamide, diclofenac, aceclofenac, acemethacin, alclofenac, bromfenac, etodolac, indometacin, nabumetone, oxametacin, proglumetacin, sulindac, tolmetin, ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, sulfinpyrazone, piroxicam, droxicam, lornoxicam, meloxicam, tenoxicam, and the COX-2 inhibitors celecoxib, etoricoxib, lumiracoxib, parecoxib, rofecoxib, valdecoxib, and pharmaceutically acceptable salts thereof.

Glucocorticoids that can be administered to a patient (e.g., a human) suffering from neurogenic inflammation in combination with a composition of the invention include, but are not limited to, hydrocortisone, cortisone acetate, prednisone, prednisolone, methylprednisolone, dexamethasone, betamethasone, triamcinolone, beclometasone, fludrocortisone acetate, deoxycorticosterone acetate, aldosterone, and pharmaceutically acceptable salts thereof.

Narcotics that can be administered to a patient (e.g., a human) suffering from neurogenic inflammation in combination with a composition of the invention include, but are not limited, to tramadol, hydrocodone, oxycodone, morphine, and pharmaceutically acceptable salts thereof.

Antiproliferative and immune modulatory agents that can be administered to a patient (e.g., a human) suffering from neurogenic inflammation in combination with a composition of the invention include, but are not limited to, alkylating agents, platinum agents, antimetabolites, topoisomerase inhibitors, dihydrofolate reductase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF-alpha agonists, TNF-alpha antagonists or scavengers, interleukin 1 (IL-1) antagonists or scavengers, endothelin A receptor antagonists, retinoic acid receptor agonists, hormonal agents, antihormonal agents, photodynamic agents, and tyrosine kinase inhibitors.

The biologically active agents can be administered prior to, concurrent with, or following administration of a composition of the invention, using any formulation, dosing, or administration known in the art that is therapeutically effective.

Formulation of Compositions

The administration of the compounds of the invention may be by any suitable means that results in the reduction of perceived pain sensation at the target region. The compounds of the invention may be contained in any appropriate amount in any suitable carrier substance, and are generally present in amounts totaling 1-99% by weight of the total weight of the composition. The composition may be provided in a dosage form that is suitable for oral, parenteral (e.g., intravenous, intramuscular), rectal, cutaneous, subcutaneous, topical, transdermal, sublingual, nasal, vaginal, intrathecal, epidural, or ocular administration, or by injection, inhalation, or direct contact with the nasal or oral mucosa.

Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The compositions may be formulated according to conventional pharmaceutical practice (see, e.g., Remington: The Science and Practice of Pharmacy, 22nd edition, 2013, ed. L. V. Allen, Pharmaceutical Press, Philadelphia, and Encyclopedia of Pharmaceutical Technology, $4^{th}$ Edition, ed. J. Swarbrick, 2013, CRC Press, New York).

Each compound may be formulated in a variety of ways that are known in the art. For example, a compound of the invention and a biologically active agent as defined herein may be formulated together or separately. Desirably, a compound of the invention and a biologically active agent are formulated together for their simultaneous or near simultaneous administration. In another embodiment, two or more biologically active agents may be formulated together with a compound of the invention, or separately. Other examples include, but are not limited to, two or more compounds of the invention formulated together, wherein the compounds are formulated together with or without one or more biologically active agents.

The individually or separately formulated agents can be packaged together as a kit. Non-limiting examples include but are not limited to kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions.

The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Controlled Release Formulations

Each compound of the invention, alone or in combination with one or more of the biologically active agents as described herein, can be formulated for controlled release (e.g., sustained or measured) administration, as described in U.S. Patent Application Publication Nos. 2003/0152637 and 2005/0025765, each incorporated herein by reference. For example, a compound of the invention, alone or in combination with one or more of the biologically active agents as described herein, can be incorporated into a capsule or tablet that is administered to the patient.

Any pharmaceutically acceptable vehicle or formulation suitable for local application and/or injection into a site to be treated (e.g., a painful surgical incision, wound, or joint), that is able to provide a sustained release of compound of the invention, alone or in combination with one or more of the biologically active agents as described herein, may be employed to provide for prolonged elimination or alleviation of inflammation, as needed. Controlled release formulations known in the art include specially coated pellets, polymer formulations or matrices for surgical insertion or as sustained release microparticles, e.g., microspheres or microcapsules, for implantation, insertion, infusion or injection, wherein the slow release of the active medicament is brought about through sustained or controlled diffusion out of the matrix and/or selective breakdown of the coating of the preparation or selective breakdown of a polymer matrix. Other formulations or vehicles for controlled, sustained, or immediate delivery of an agent to a preferred localized site in a patient include, e.g., suspensions, emulsions, gels, liposomes and any other suitable art known delivery vehicle or formulation acceptable for subcutaneous or intramuscular administration.

A wide variety of biocompatible materials may be utilized as a controlled release carrier to provide the controlled release of a compound of the invention, alone or in combination with one or more biologically active agents, as described herein. Any pharmaceutically acceptable biocompatible polymer known to those skilled in the art may be utilized. It is preferred that the biocompatible controlled release material degrade in vivo within about one year, preferably within about 3 months, more preferably within about two months. More preferably, the controlled release material will degrade significantly within one to three months, with at least 50% of the material degrading into non-toxic residues, which are removed by the body, and 100% of the compound of the invention being released within a time period within about two weeks, preferably within about 2 days to about 7 days. A degradable controlled release material should preferably degrade by hydrolysis, either by surface erosion or bulk erosion, so that release is not only sustained but also provides desirable release rates. However, the pharmacokinetic release profile of these formulations may be first order, zero order, bi- or multi-phasic, to provide the desired reversible local anti-nociceptive effect over the desired time period.

Suitable biocompatible polymers can be utilized as the controlled release material. The polymeric material may comprise biocompatible, biodegradable polymers, and, in certain preferred embodiments, is preferably a copolymer of lactic and glycolic acid. Preferred controlled release materials which are useful in the formulations of the invention include the polyanhydrides, polyesters, co-polymers of lactic acid and glycolic acid (preferably wherein the weight ratio of lactic acid to glycolic acid is no more than 4:1 i.e., 80% or less lactic acid to 20% or more glycolic acid by weight) and polyorthoesters containing a catalyst or degradation enhancing compound, for example, containing at least 1% by weight anhydride catalyst such as maleic anhydride. Examples of polyesters include polylactic acid, polyglycolic acid and polylactic acid-polyglycolic acid copolymers. Other useful polymers include protein polymers such as collagen, gelatin, fibrin and fibrinogen and polysaccharides such as hyaluronic acid.

The polymeric material may be prepared by any method known to those skilled in the art. For example, where the polymeric material is comprised of a copolymer of lactic and glycolic acid, this copolymer may be prepared by the procedure set forth in U.S. Pat. No. 4,293,539, incorporated herein by reference. Alternatively, copolymers of lactic and glycolic acid may be prepared by any other procedure known to those skilled in the art. Other useful polymers include polylactides, polyglycolides, polyanhydrides, polyorthoesters, polycaprolactones, polyphosphazenes, polyphosphoesters, polysaccharides, proteinaceous polymers, soluble derivatives of polysaccharides, soluble derivatives of proteinaceous polymers, polypeptides, polyesters, and polyorthoesters or mixtures or blends of any of these.

Pharmaceutically acceptable polyanhydrides which are useful in the present invention have a water-labile anhydride linkage. The rate of drug release can be controlled by the particular polyanhydride polymer utilized and its molecular weight. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, derivatives of hydrolyzed amylopectin such as hydroxyethyl starch (HES), hydroxyethyl amylose, dialdehyde starch, and the like. The polyanhydride polymer may be branched or linear.

Examples of polymers which are useful in the present invention include (in addition to homopolymers and copolymers of poly(lactic acid) and/or poly(glycolic acid)) poly[bis(p-carboxyphenoxy) propane anhydride] (PCPP), poly[bis(p-carboxy)methane anhydride](PCPM), polyanhydrides of oligomerized unsaturated aliphatic acids, polyanhydride polymers prepared from amino acids which are modified to include an additional carboxylic acid, aromatic polyanhydride compositions, and co-polymers of polyanhydrides with other substances, such as fatty acid terminated polyanhydrides, e.g., polyanhydrides polymerized from monomers of dimers and/or trimers of unsaturated fatty acids or unsaturated aliphatic acids. Polyanhydrides may be prepared in accordance with the methods set forth in U.S. Pat. No. 4,757,128, incorporated herein by reference. Polyorthoester polymers may be prepared, e.g., as set forth in U.S. Pat. No. 4,070,347, incorporated herein by reference. Polyphosphoesters may be prepared and used as set forth in U.S. Pat. Nos. 6,008,318, 6,153,212, 5,952,451, 6,051,576, 6,103,255, 5,176,907 and 5,194,581, each of which is incorporated herein by reference.

Proteinaceous polymers may also be used. Proteinaceous polymers and their soluble derivatives include gelation biodegradable synthetic polypeptides, elastin, alkylated collagen, alkylated elastin, and the like. Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-valine, L-tyrosine, and the like.

In additional embodiments, the controlled release material, which in effect acts as a carrier for a compound of the invention, alone or in combination with one or more biologically active agents as described herein, can further include a bioadhesive polymer such as pectins (polygalacturonic acid), mucopolysaccharides (hyaluronic acid, mucin) or non-toxic lectins or the polymer itself may be bioadhesive, e.g., polyanhydride or polysaccharides such as chitosan.

In embodiments where the biodegradable polymer comprises a gel, one such useful polymer is a thermally gelling polymer, e.g., polyethylene oxide, polypropylene oxide (PEO-PPO) block copolymer such as Pluronic™ F127 from BASF Wyandotte. In such cases, the local anesthetic formulation may be injected via syringe as a free-flowing liquid, which gels rapidly above 30° C. (e.g., when injected into a patient). The gel system then releases a steady dose of a compound of the invention, alone or in combination with one or more biologically active agents as described herein, at the site of administration.

Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, taste masking agents (such as hydroxypropyl methylcellulose, hydroxypropyl cellulose), and the like.

One or more compounds of the invention and one or more biologically active agents, as defined herein, may be mixed together in a tablet, capsule, or other vehicle, or may be partitioned. In one example, a compound of the invention is contained on the inside of the tablet, and the biologically active agent is on the outside of the tablet, such that a substantial portion of the biologically active agent is released prior to the release of the compound of the invention.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Formulations for oral administration to the mouth may also be provided as a mouthwash, an oral spray, oral rinse solution, or oral ointment or oral gel.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the patient. Chronic, long-term administration will be indicated in many cases.

Parenteral Formulations

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilizers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 µg/ml, for example from about 10 ng/ml to about 1 g/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Topical Formulations

The compositions of the invention, alone or in combination with one or more of the biologically active agents described herein, can also be adapted for topical use with a topical vehicle containing from between 0.0001% and 25% (w/w) or more of active ingredient(s).

In a preferred combination, the active ingredients are preferably each from between 0.0001% to 10% (w/w), more preferably from between 0.0005% to 4% (w/w) active agent. The topical formulation, including but not limited to a cream, gel, or ointment, can be applied one to four times daily, or as needed. Performing the methods described herein, the topical vehicle containing the composition of the invention, or a combination therapy containing a composition of the invention is preferably applied to the site of inflammation on the patient. For example, a cream may be applied to the hands of a patient suffering from arthritic fingers.

The compositions can be formulated using any dermatologically acceptable carrier. Exemplary carriers include a solid carrier, such as alumina, clay, microcrystalline cellulose, silica, or talc; and/or a liquid carrier, such as an alcohol, a glycol, or a water-alcohol/glycol blend. The therapeutic agents may also be administered in liposomal formulations that allow therapeutic agents to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; 8,822,537, and PCT Publication No. WO 96/40061. Examples of other appropriate vehicles are described in U.S. Pat. Nos. 4,877,805, 8,822,537, and EP Publication No. 0586106A1. Suitable vehicles of the invention may also include mineral oil, petrolatum, polydecene, stearic acid, isopropyl myristate, polyoxyl 40 stearate, stearyl alcohol, or vegetable oil.

The composition can further include a skin penetrating enhancer, such as those described in "Percutaneous Penetration enhancers", (eds. Smith E W and Maibach H I. CRC Press 1995). Exemplary skin penetrating enhancers include alkyl (N,N-disubstituted amino alkanoate) esters, such as dodecyl 2-(N,N dimethylamino) propionate (DDAIP), which is described in patents U.S. Pat. Nos. 6,083,996 and 6,118,020, which are both incorporated herein by reference; a water-dispersible acid polymer, such as a polyacrylic acid polymer, a carbomer (e.g., Carbopol™ or Carbopol 940P™, available from B. F. Goodrich Company (Akron, Ohio)), copolymers of polyacrylic acid (e.g., Pemulen™ from B. F. Goodrich Company or Polycarbophil™ from A. H. Robbins, Richmond, Va.; a polysaccharide gum, such as agar gum, alginate, carrageenan gum, ghatti gum, karaya gum, kadaya gum, rhamsan gum, xanthan gum, and galactomannan gum (e.g., guar gum, carob gum, and locust bean gum), as well as other gums known in the art (see for instance, Industrial Gums: Polysaccharides & Their Derivatives, Whistler R. L., BeMiller J. N. (eds.), 3rd Ed. Academic Press (1992) and Davidson, R. L., Handbook of Water-Soluble Gums & Resins, McGraw-Hill, Inc., N.Y. (1980)); or combinations thereof.

Other suitable polymeric skin penetrating enhancers are cellulose derivatives, such as ethyl cellulose, methyl cellulose, hydroxypropyl cellulose. Additionally, known transdermal penetrating enhancers can also be added, if desired. Illustrative are dimethyl sulfoxide (DMSO) and dimethyl acetamide (DMA), 2-pyrrolidone, N,N-diethyl-m-toluamide (DEET), 1-dodecylazacycloheptane-2-one (Azone™, a registered trademark of Nelson Research), N,N-dimethylformamide, N-methyl-2-pyrrolidone, calcium thioglycolate and other enhancers such as dioxolanes, cyclic ketones, and their derivatives and so on.

Also illustrative are a group of biodegradable absorption enhancers which are alkyl N,N-2-(disubstituted amino) alkanoates as described in U.S. Pat. Nos. 4,980,378 and 5,082,866, which are both incorporated herein by reference, including: tetradecyl (N,N-dimethylamino) acetate, dodecyl (N,N-dimethylamino) acetate, decyl (N,N-dimethylamino) acetate, octyl (N,N-dimethylamino) acetate, and dodecyl (N,N-diethylamino) acetate.

Particularly preferred skin penetrating enhancers include isopropyl myristate; isopropyl palmitate; dimethyl sulfoxide; decyl methyl sulfoxide; dimethylalanine amide of a medium chain fatty acid; dodecyl 2-(N,N-dimethylamino) propionate or salts thereof, such as its organic (e.g., hydrochloric, hydrobromic, sulfuric, phosphoric, and nitric acid addition salts) and inorganic salts (e.g., acetic, benzoic, salicylic, glycolic, succinic, nicotinic, tartaric, maleic, malic, pamoic, methanesulfonic, cyclohexanesulfamic, picric, and lactic acid addition salts), as described in U.S. Pat. No. 6,118,020; and alkyl 2-(N,N-disubstituted amino)-alkanoates, as described in U.S. Pat. Nos. 4,980,378 and 5,082,866.

The skin penetrating enhancer in this composition by weight would be in the range of 0.5% to 10% (w/w). The most preferred range would be between 1.0% and 5% (w/w). In another embodiment, the skin penetrating enhancer comprises between 0.5%-1%, 1%-2%, 2%-3%, 3%-4%, or 4%-5%, (w/w) of the composition.

The compositions can be provided in any useful form. For example, the compositions of the invention may be formulated as solutions, emulsions (including microemulsions), suspensions, creams, ointments, foams, lotions, gels, powders, or other typical solid, semi-solid, or liquid compositions (e.g., topical sprays) used for application to the skin or other tissues where the compositions may be used. Such compositions may contain other ingredients typically used in such products, such as colorants, fragrances, thickeners (e.g., xanthan gum, a fatty acid, a fatty acid salt or ester, a fatty alcohol, a modified cellulose, a modified mineral material, Krisgel 100™, or a synthetic polymer), antimicrobials, solvents, surfactants, detergents, gelling agents, antioxidants, fillers, dyestuffs, viscosity-controlling agents, preservatives, humectants, emollients (e.g., natural or synthetic oils, hydrocarbon oils, waxes, or silicones), hydration agents, chelating agents, demulcents, solubilizing excipients, adjuvants, dispersants, skin penetrating enhancers, plasticizing agents, preservatives, stabilizers, demulsifiers, wetting agents, sunscreens, emulsifiers, moisturizers, astringents, deodorants, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

The compositions can also include other like ingredients to provide additional benefits and improve the feel and/or appearance of the topical formulation. Specific classes of additives commonly use in these formulations include: isopropyl myristate, sorbic acid NF powder, polyethylene glycol, phosphatidylcholine (including mixtures of phosphatidylcholine, such as phospholipon G), Krisgel 100™ distilled water, sodium hydroxide, decyl methyl sulfoxide (as a skin penetrating enhancer), menthol crystals, lavender oil, butylated hydroxytoluene, ethyl diglycol reagent, and 95% percent (190 proof) ethanol.

Formulations for Ophthalmic Administration

The compounds of the invention can also be formulated with an ophthalmically acceptable carrier in sufficient concentration so as to deliver an effective amount of the active compound or compounds to the optic nerve site of the eye. Preferably, the ophthalmic, therapeutic solutions contain one or more of the active compounds in a concentration range of approximately 0.0001% to approximately 5% (weight by volume) and more preferably approximately 0.0005% to approximately 0.1% (weight by volume).

An ophthalmically acceptable carrier does not cause significant irritation to the eye and does not abrogate the pharmacological activity and properties of the charged sodium channel blockers.

Ophthalmically acceptable carriers are generally sterile, essentially free of foreign particles, and generally have a pH in the range of 5-8. Preferably, the pH is as close to the pH of tear fluid (7.4) as possible. Ophthalmically acceptable carriers are, for example, sterile isotonic solutions such as isotonic sodium chloride or boric acid solutions. Such carriers are typically aqueous solutions contain sodium chloride or boric acid. Also useful are phosphate buffered saline (PBS) solutions.

Various preservatives may be used in the ophthalmic preparation. Preferred preservatives include, but are not limited to, benzalkonium potassium, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose and hydroxyethyl cellulose.

Tonicity adjustors may be added as needed or convenient. They include, but are not limited to, salts, particularly sodium chloride, potassium chloride, etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed. Ophthalmically acceptable antioxidants can also be include. Antioxidants include but are not limited to sodium metabisulfite, sodium thiosulfate, acetylcysteine, butylated hydroxyanisole, and butylated hydroxytoluene.

Formulations for Nasal and Inhalation Administration

The pharmaceutical compositions of the invention can be formulated for nasal or intranasal administration. Formulations suitable for nasal administration, when the carrier is a solid, include a coarse powder having a particle size, for example, in the range of approximately 20 to 500 microns which is administered by rapid inhalation through the nasal passage. When the carrier is a liquid, for example, a nasal spray or as nasal drops, one or more of the formulations can be admixed in an aqueous or oily solution and inhaled or sprayed into the nasal passage.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount, Capsules and cartridges of, for example, gelatin for use in an inhaler or insufflator can be formulated containing a powder mix of the compound and a suitable powder base such as lactose or starch.

Dry powder compositions for topical delivery to the lung by inhalation may, for example, be presented in capsules and cartridges of, for example, gelatin or blisters of, for example, laminated aluminum foil, for use in an inhaler or insufflator. Powder blend formulations generally contain a powder mix for inhalation of the compound of the invention and a suitable powder base (carrier/diluent/excipient substance) such as mono-, di or ploy-saccharides (e.g. lactose or starch). Use of lactose is preferred. In one embodiment, each capsule or cartridge may contain between about 2 ug to about 100 mg of the compound of formula (I) optionally in combination with another therapeutically active ingredient. In a preferred embodiment, each capsule or cartridge may contain between about 10 ug to about 50 mg of the compound of formula (I) optionally in combination with another therapeutically active ingredient. In another embodiment, each capsule or cartridge may contain between about 20 ug to about 10 mg of the compound of formula (I) optionally in combination with another therapeutically active ingredient. Alternatively, the compound of the invention may be delivered without excipients.

Suitably, the packaging/medicament dispenser is of a type selected from the group consisting of a reservoir dry powder inhaler (RDPI), a multi-dose dry powder inhaler (MDPI), and a metered dose inhaler (MDI).

Solutions or suspensions for use in a pressurized container, pump, spray, atomizer, or nebulizer can be formulated to contain an aqueous medium, ethanol, aqueous ethanol, or a suitable alternative agent for dispersing, solubilizing, or extending release of the active ingredient(s); a propellant as solvent; and/or a surfactant, such as sorbitan trioleate, oleic acid, or an oligolactic acid.

Compositions formulated for nasal or inhalation administration may include one or more taste-masking agents such as flavoring agents, sweeteners, and other strategies, such as sucrose, dextrose, and lactose, carboxylic acids, menthol, amino acids or amino acid derivatives such as arginine, lysine, and monosodium glutamate, and/or synthetic flavor oils and flavoring aromatics and/or natural oils, extracts from plants, leaves, flowers, fruits, etc. and combinations thereof. These may include cinnamon oils, oil of wintergreen, peppermint oils, clover oil, bay oil, anise oil, eucalyptus, vanilla, citrus oil such as lemon oil, orange oil, grape and grapefruit oil, fruit essences including apple, peach, pear, strawberry, raspberry, cherry, plum, pineapple, apricot, etc. Additional sweeteners include sucrose, dextrose, aspartame, acesulfame-K, sucralose and saccharin, organic acids (by non-limiting example citric acid and aspartic acid). Such flavors may be present at from about 0.05 to about 4 percent by weight, and may be present at lower or higher amounts as a factor of one or more of potency of the effect on flavor, solubility of the flavorant, effects of the flavorant on solubility or other physicochemical or pharmacokinetic properties of other formulation components, or other factors.

Indications

The compounds, compositions, methods, and kits of the invention can be used to treat pain, cough or itch associated with any of a number of conditions, including trigeminal trophic syndrome, erythromelalgia, back and neck pain, lower back pain, cancer pain, gynecological and labor pain, abdominal wall pain, chronic abdominal wall pain, fibromyalgia, allergic rhinitis, arthritis, rheumatoid arthritis, osteoarthritis, rheumatological pains, orthopedic pains, acute and post herpetic neuralgia and other neuropathic pains (including peripheral neuropathy), sickle cell crises, muscle pain, vulvodynia, rectal pain, Levator ani syndrome, proctalgia fugax, peri-anal pain, hemorrhoid pain, stomach pain, ulcers, inflammatory bowel disease, irritable bowel disease, irritable bowel syndrome, oral mucositis, esophagitis, interstitial cystitis, urethritis and other urological pains, dental pain, burn pain, headaches, ophthalmic irritation, conjunctivitis (e.g., allergic conjunctivitis), eye redness, dry eye, dry eye syndrome (chronic ocular pain), complex regional pain syndrome, acute postoperative pain, postoperative pain, post-surgical ocular pain, and procedural pain (i.e., pain associated with injections, draining an abscess, surgery, dental procedures, ophthalmic procedures, ophthalmic irritation, conjunctivitis (e.g., allergic conjunctivitis), eye redness, dry eye, arthroscopies and use of other medical instrumentation, cosmetic surgical procedures, dermatological procedures, setting fractures, biopsies, and the like).

Since a subclass of nociceptors mediate itch sensation, the compounds, compositions, methods, and kits of the invention can also be used to treat itch in patients with conditions like pruritus (including, but not limited to, brachioradial, chronic idiopathic, genital/anal, notalgia paresthetica, and scalp), allergic dermatitis, atopic dermatitis, contact dermatitis, poison ivy, infections, parasites, insect bites, pregnancy, metabolic disorders, liver or renal failure, drug reactions, allergic reactions, eczema, hand eczema, genital and anal itch, hemorrhoid itch, and cancer.

Since a subclass of nociceptors can initiate aberrant cough reflexes, the compounds, compositions, methods, and kits of the invention can also be used to treat cough in patients with conditions like asthma, COPD, asthma-COPD overlap syndrome (ACOS), interstitial pulmonary fibrosis (IPF), idiopathic pulmonary fibrosis, post viral cough, post-infection cough, chronic idiopathic cough and lung cancer.

The compounds, compositions, methods, and kits of the invention can also be used to treat neurogenic inflammation and neurogenic inflammatory disorders. Inflammation is a complex set of responses to harmful stimuli that results in localized redness, swelling, and pain. Inflammation can be innate or adaptive, the latter driven by antigens and is mediated by immune cells (immune-mediated inflammation). Neurogenic inflammation results from the efferent functions of pain-sensing neurons (nociceptors), wherein neuropeptides and other chemicals that are pro-inflammatory mediators are released from the peripheral terminals of the nociceptors when they are activated. This release process is mediated by calcium influx and exocytosis of peptide containing vesicles, and the pro-inflammatory neuropeptides include substance P, neurokinin A and B (collectively known as tachykinins), calcitonin gene-related peptide (CGRP), and vasoactive intestinal polypeptide (VIP).

The release of peripheral terminal chemicals stimulate a variety of inflammatory responses. First, the release of substance P can result in an increase in capillary permeability such that plasma proteins leak from the intravascular compartment into the extracellular space (plasma extravasation), causing edema. This can be detected as a wheal (a firm, elevated swelling of the skin) which is one component of a triad of inflammatory responses-wheal, red spot, and flare-known as the Lewis triple response. Second, the release of CGRP causes vasodilation, leading to increased blood flow. This can be detected as a flare, which is another component of the Lewis triple response.

Substance P also has a pro-inflammatory action on immune cells (e.g. macrophages, T-cells, mast cells, and dendritic cells) via their neurokinin-1 (NK1) receptor. This effect has been documented in allergic rhinitis, gastritis, and colitis, and represents an interface between the neurogenic and immune-mediated components of inflammation. Substance P released from one nociceptor may also act on NK1 receptors on neighboring nociceptors to sensitize or activate them, causing a spread of activation and afferent/efferent function. These efferent functions of nociceptors can be triggered by: 1) Direct activation of a nociceptor terminal by a peripheral adequate stimulus applied to the terminal (e.g. a pinch); 2) Indirect antidromic activation of a non-stimulated nociceptor terminal by the axon reflex, wherein action potential input from one terminal of a nociceptor, upon reaching a converging axonal branch point in the periphery, results in an action potential traveling from the branch point down to the peripheral terminal of a non-stimulated terminal; and 3) Activation as a result of activity in nociceptor central terminals in the CNS traveling to the periphery (e.g., primary afferent depolarization of central terminals produced by GABA can be sufficient to initiate action potentials traveling the "wrong way").

Genomic analysis of lung resident ILC2 cells has revealed expression of receptors for several neuropeptides released by sensory neurons, including SP, CGRP and VIP, providing an opportunity for nociceptors to directly communicate with these cells. In particular, VIP is found to be expressed in NaV1.8+ nodose ganglion neurons, including lung afferents in OVA-exposed mice. Cultured nodose ganglion neurons stimulated with capsaicin or IL5 also released VIP while BALF from OVA-exposed mice contained elevated VIP compared to vehicle-challenged mice (Talbot et al., Neuron. 2015 Jul. 15; 87(2): 341-354). These data indicate that VIP is released in the inflamed lung and can be blocked by silencing neurons with charged sodium channel blockers of the present invention. In addition, when CD4+ T cells cultured under $T_H2$ skewing conditions were exposed to recombinant mouse VIP, the transcript levels of IL-13 and IL-5 increased, suggesting that VIP contributes to the competence of $T_H2$ cells to transcribe these type II regulatory cytokines.

Immune mediator release from immune cells can also activate nociceptors. Mast cells are found close to primary nociceptive neurons and contribute to nociceptor sensitization in a number of contexts. Injection of the secretagogue compound 48/80 promotes degranulation of mast cells in the dura and leads to excitation of meningeal nociceptors. Mast cell degranulation also contributes to the rapid onset of nerve growth factor-induced thermal hyperalgesia. Macrophages contribute to nociceptor sensitization by releasing several soluble mediators. Expression of the chemokine macrophage inflammatory protein-1α (MIP-1α) and its receptors CCR1 and CCR5 is increased in macrophages and Schwann cells after partial ligation of the sciatic nerve and contributes to the development of neuropathic pain. Lymphocytes contribute to the sensitization of peripheral nociceptors. T cells infiltrate the sciatic nerve and dorsal root ganglion (DRG) after nerve injury. Hyperalgesia and allodynia induced by nerve injury are markedly attenuated or abrogated in rodents lacking T cells and the immunosuppressant rapamycin attenuates neuropathic pain in rats, partly owing to an effect on T cells. Among the subsets of T cells, type 1 and 2 helper T cells ($T_H1$ and $T_H2$ cells) have been shown to have different roles in neuropathic pain. $T_H1$ cells facilitate neuropathic pain behavior by releasing proinflammatory cytokines (IL-2 and interferon-γ (IFNγ)), whereas $T_H2$ cells inhibit it by releasing anti-inflammatory cytokines (IL-4, IL-10 and IL-13). The complement system also has a role in inflammatory hyperalgesia and neuropathic pain. C5a, an anaphylatoxin, is an important effector of the complement cascade and upon binding to C5aR1 receptors on neutrophils it becomes a potent neutrophil attractant (Ren & Dubner, *Nat. Med.* 16:1267-1276 (2010)).

Bacterial infections have been shown to directly activate nociceptors, and that the immune response mediated through TLR2, MyD88, T cells, B cells, and neutrophils and monocytes is not necessary for *Staphylococcus aureus*-induced pain in mice (Chiu et al., Nature 501:52-57 (2013)). Mechanical and thermal hyperalgesia in mice is correlated with live bacterial load rather than tissue swelling or immune activation. Bacteria induce calcium flux and action potentials in nociceptor neurons, in part via bacterial N-formylated peptides and the pore-forming toxin α-haemolysin, through distinct mechanisms. Specific ablation of Nav1.8-lineage neurons, which include nociceptors, abrogated pain during bacterial infection, but concurrently increased local immune infiltration and lymphadenopathy of the draining lymph node. Thus, bacterial pathogens produce pain by directly activating sensory neurons that modulate inflammation, an unsuspected role for the nervous system in host-pathogen interactions. Data from Talbot et al., (Neuron. 2015 Jul. 15; 87(2): 341-354.) have also suggested that nociceptors are activated during exposure to allergens in sensitized animals.

In certain disorders, neurogenic inflammation contributes to the peripheral inflammation elicited by tissue injury, autoimmune disease, infection, and exposure to irritants in soft tissue, skin, the respiratory system, joints, the urogenital and GI tract, the liver, and the brain. Neurogenic inflammatory disorders include, but are not limited to, allergic inflammation, inflammatory bowel disease, interstitial cystitis, atopic dermatitis, asthma, conjunctivitis, arthritis, colitis, contact dermatitis, diabetes, eczema, cystitis, gastritis, migraine headache, psoriasis, rhinitis, rosacea, sunburn, pancreatitis, chronic cough, chronic rhinosinusistis, traumatic brain injury, polymicrobial sepsis, tendinopathies, chronic urticaria, rheumatic disease, acute lung injury, exposure to irritants, inhalation of irritants, pollutants, or chemical warfare agents, as described herein.

Assessment of Pain, Cough, Itch, and Neurogenic Inflammation

In order to measure the efficacy of any of the compounds, compositions, methods, and kits of the invention in the treatment of pain associated with musculoskeletal, immunoinflammatory and neuropathic disorders, a measurement index may be used. Indices that are useful include a visual analog scale (VAS), a Likert scale, categorical pain scales, descriptors, the Lequesne index, the WOMAC index, and the AUSCAN index, each of which is well known in the art. Such indices may be used to measure pain, itch, function, stiffness, or other variables.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain or itch by choosing the spot on the line that best corresponds to the sensation of pain or itch, where one end of the line corresponds to "no pain" (score of 0 cm) or "no itch" and the other end of the line corresponds to "unbearable pain" or "unbearable itch" (score of 10 cm). This procedure provides a simple and rapid approach to obtaining quantitative information about how the patient is experiencing pain or itch. VAS scales and their use are described, e.g., in U.S. Pat. Nos. 6,709,406 and 6,432,937.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced. Likert scales and their use are described, e.g., in U.S. Pat. Nos. 6,623,040 and 6,766,319.

The Lequesne index and the Western Ontario and McMaster Universities (WOMAC) osteoarthritis index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert. Both the WOMAC index and the Lequesne index questionnaires have been extensively validated in OA, including in surgical settings (e.g., knee and hip arthroplasty). Their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index may utilize, e.g., a Likert or a VAS scale.

Indices that are useful in the methods, compositions, and kits of the invention for the measurement of pain include the Pain Descriptor Scale (PDS), the Visual Analog Scale (VAS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

Itch can be measured by subjective measures (VAS, Lickert, descriptors). Another approach is to measure scratch which is an objective correlate of itch using a vibration transducer or movement-sensitive meters.

Cough can be measured by standard questionnaires like the Leicester Cough Questionnaire as well as validated objective instruments to measure cough frequency (e.g. VitaloJAK).

EXAMPLES

The following examples are intended to illustrate the invention and are not intended to limit it.

Example 1—Synthesis of Compounds 1A' to 6A'

General Abbreviation Definitions

ACN acetonitrile aq. aqueous

CDCl3 $D_3$-chloroform

δ chemical shift (ppm)

DCM dichloromethane

DMSO dimethyl sulfoxide

ESI electrospray ionization $Et_2O$ diethyl ether

EtOAc ethyl acetate h hour

MeOH methanol mHz megahertz

MS mass spectrometry m/z mass to charge ratio

NMR nuclear magnetic resounance

RT room temperature

TLC thin layer chromatography

UV ultraviolet light i. Synthesis of 1-benzyl-1-(2-((2, 6-dimethyiphenyl) amino)-2-oxoethyl) piperidin-1-ium Bromide

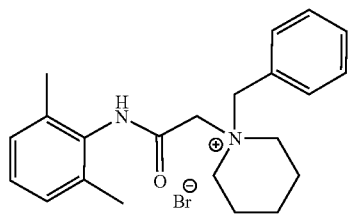 [SMILES: Cc1cccc(C)c1NC(=O)C[N+]1(Cc2ccccc2)CCCCC1 ; [Cl-]]

Compound 1'A

Synthesis of Intermediate 2-bromo-N-(2,6-dimethylphenyl)acetamide

To a suspension of 2, 6-dimethylaniline (30.5 mL, 247.56 mmol, 1.0 eq) in water (300 mL) was added bromoacetyl bromide (23.8 mL, 272.31 mmol, 1.1 eq) at 10° C. The reaction mixture was maintained at pH 9-10 with 15% Na2CO3 (aq.) solution for 1 hour as the progress of the reaction was monitored by TLC (mobile phase: 30% EtOAc in hexane, visualization by UV). The reaction mixture was extracted with EtOAc (2×600 mL) and the combined organic extracts were washed with brine (200 mL), dried over Na2SO4, filtered and concentrated under reduced pressure. The resulting crude product was triturated with Et2O (2×200 mL) to afford 2-bromo-N-(2, 6-dimethylphenyl) acetamide (21 g) as a white solid. MS (ESI): m/z 244.02 [M+2]+. 1H NMR (400 MHz, CDCl3) δ 7.75 (br s, 1H), 7.20-7.02 (m, 3H), 4.07 (s, 2H), 2.24 (s, 6H).

Synthesis of Intermediate N-(2, 6-dimethylphenyl)-2-(piperidin-1-yl) acetamide

To a stirred solution of 2-bromo-N-(2,6-dimethylphenyl) acetamide (1.2 g, 5.0 mmol, 1.0 eq) in EtOAc (40 mL) was added piperidine (0.851 g, 10.0 mmol, 2.0 eq), and the reaction mixture was stirred for 16 h at 75° C. as the progress of the reaction was monitored by TLC (mobile phase: 50% EtOAc in petrolium ether, visualization by UV). The reaction mixture was diluted with EtOAc (20 mL) and washed with water (2×50 ml). The organic extracts were combined, dried over $Na_2SO_4$, filtered and concentrated under reduced pressure to afford crude product, which was triturated with n-pentane (25 mL) and dried under vacuo to afford product N-(2, 6-dimethylphenyl)-2-(piperidin-1-yl) acetamide (1.05 g). MS (ESI): m/z 247.36 [M+H]+. $^1$H NMR (400 MHz, CDCl3-d) δ ppm 8.81 (1H, br s), 7.04-7.11 (3H, m), 3.14 (2H, s), 2.62 (4H, br s), 2.24 (6H, s), 1.65 (4H, quin, J=5.61 Hz), 1.44-1.54 (2H, m).

Synthesis of 1-benzyl-1-(2-((2, 6-dimethylphenyl) amino)-2-oxoethyl) piperidin-1-ium Bromide To a stirred solution of N-(2,6-dimethylphenyl)-2-(piperidin-1-yl) acetamide (0.15 g, 0.6 mmol, 1.0 eq) in ACN (3 mL) was added benzyl bromide (0.205 g, 1.2 mmol, 2.0 eq), and the reaction mixture was stirred for 16 h at 80° C. in a sealed tube as progress of the reaction was monitored by TLC (mobile phase: 10% MeOH in DCM, visualization by UV). The reaction mixture was allowed to cool to room temperature and concentrated under reduced pressure to afford crude product, which was triturated with EtOAc (15 mL) and dried under vacuo to afford product 1-benzyl-1-(2-((2,6-dimethylphenyl)amino)-2-oxoethyl)piperidin-1-ium bromide (0.15 g). MS (ESI): m/z 337.2 [M]+. ¹H NMR (400 MHz, DMSO-d₆) δ ppm 10.07 (1H, s), 7.49-7.66 (5H, m), 7.07-7.21 (3H, m), 4.96 (2H, s), 4.21 (2H, s), 3.65 (2H, br d, J=12.50 Hz), 3.50 (2 H, dt, J=12.93, 6.69 Hz), 2.21 (6H, s), 1.91-2.05 (4H, m), 1.64-1.76 (1H, m), 1.55 (1H, dt, J=13.76, 7.04 Hz).

ii. Synthesis of 1-benzyl-1-(2-((2, 6-dimethylphenyl)amino)-2-oxoethyl) pyrrolidin-1-ium Bromide

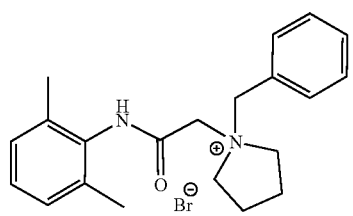

Compound 2'A

Synthesis of Intermediate N-(2, 6-dimethylphenyl)-2-(pyrrolidin-1-yl)acetamide To a stirred solution of 2-bromo-N-(2,6-dimethylphenyl) acetamide (1.2 g, 5.0 mmol, 1.0) in EtOAc (40 mL) was added pyrrolidine (0.533 g, 7.5 mmol, 1.5 eq), and the reaction mixture was stirred for 3 h at 75° C. as the progress of the reaction was monitored by TLC (mobile phase: 50% EtOAc in petrolium ether, visualization by UV). The reaction mixture was diluted with EtOAc (25 mL), washed with water (50 mL), dried over NaSO4, filtered and concentrated under reduced pressure to afford N-(2, 6-dimethylphenyl)-2-(pyrrolidin-1-yl) acetamide (1.0 g). MS (ESI): m/z 233.44 [M+H]+. ¹H NMR (400 MHz, CDCl3-d) δ ppm 8.63 (1H, br s), 7.00-7.15 (3H, m), 3.35 (2H, s), 2.69-2.84 (4H, m), 2.24 (6H, s), 1.80-1.93 (4H, m).

Synthesis of 1-benzyl-1-(2-((2, 6-dimethylphenyl)amino)-2-oxoethyl) pyrrolidin-1-ium Bromide To a stirred solution of N-(2, 6-dimethylphenyl)-2-(pyrrolidin-1-yl) acetamide (0.15 g, 0.6 mmol, 1.0 eq) in ACN (5 mL) added benzyl bromide (0.205 g, 1.2 mmol, 2.0 eq), and the reaction mixture was stirred for 16 h at 80° C. in a sealed tube as progress of the reaction was monitored by TLC (mobile phase: 10% MeOH in DCM, visualization by UV). The reaction cooled to room temperature and was concentrated under reduced pressure to afford crude product, which was triturated with EtOAc (15 mL) and dried under vacuo to afford 1-benzyl-1-(2-((2, 6-dimethylphenyl) amino)-2-oxoethyl) pyrrolidin-1-ium bromide (0.14 g). MS (ESI): m/z 323.2 [M]+. ¹H NMR (400 MHz, DMSO-d₆) δ ppm 2.11-2.29 (10H, m), 3.60-3.74 (2H, m), 3.76-3.88 (2H, m), 4.20 (2H, s), 4.83 (2H, s), 7.08-7.18 (3H, m), 7.50-7.66 (5H, m), 9.97 (1H, s).

iii. Synthesis of 1-benzyl-1-(1-((2,6-dimethylphenyl)amino)-1-oxobutan-2-yl)piperidin-1-iumbromide

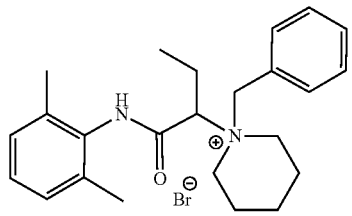 [SMILES: CCC(C(=O)Nc1c(C)cccc1C)[N+]1(Cc2ccccc2)CCCCC1 ; [Cl-]]

Compound 3'A

Synthesis of Intermediate 2-bromobutanoyl Chloride

Thionyl chloride (150 mL) was added to 2-bromobutanoic acid (25 g, 149.7 mmol, 1.0 eq) at 0° C. and the resulting solution was subsequently stirred at 80° C. for 2 h. The reaction mixture was cooled to RT and concentrated under reduced pressure to afford crude 2-bromobutanoyl chloride (27.7 g, 99.5%) as a brown residue which was taken to next step immediately without further purification. ¹H NMR (400 MHz, CDCl₃) δ 4.52-4.44 (m, 1H), 2.29-2.16 (m, 1H), 2.15-2.02 (m, 1H), 1.10 (t, J=7.3 Hz, 3H).

Synthesis of Intermediate 2-bromo-N-(2, 6-dimethylphenyl) butanamide

A solution of 2, 6-dimethylaniline (15 g, 121.18 mmol, 1.0 eq) and pyridine (15 mL, 189.6 mmol, 1.5 eq) in DCM (400 mL) was cooled in an ice bath to 0° C. To this mixture was slowly added a solution of 2-bromobutanoyl chloride (27.5 g, 148.6 mmol, 1.2 eq) in DCM (50 mL) and the resulting mixture was allowed to warm to room temperature while stirring for 2 h. The reaction solution was adjusted to pH~5 to 6 with 2 N HCl and extracted with DCM (2×200 mL). The combined organic extracts were washed with water (250 mL) and brine (200 mL), dried over Na₂SO₄, filtered and concentrated under reduced pressure. The resulting crude product was triturated with n-pentane (150 mL) to afford 2-bromo-N-(2,6-dimethylphenyl)butanamide (30 g). MS (ESI): m/z 272.13 [M+2]+. ¹H NMR (400 MHz, DMSO-d₆) δ 9.69 (s, 1H), 7.15-7.02 (m, 3H), 4.51 (t, J=7.3 Hz, 1H), 2.22-2.04 (m, 7H), 2.03-1.91 (m, 1H), 0.98 (t, J=7.3 Hz, 3H).

Synthesis of Intermediate N-(2, 6-dimethylphenyl)-2-(piperidin-1-yl) butanamide To a stirred solution of 2-bromo-N-(2,6-dimethylphenyl) butanamide (50 g, 259.1 mmol, 1.0 eq) in toluene (1 L) was added piperidine (54 mL, 544.1 mmol, 2.1 eq) at RT. The reaction mixture was stirred at 110° C. for 16 h as progress of the reaction was monitored by TLC (mobile phase: 30% EtOAc in hexane, visualization by UV). The reaction mixture was concentrated under reduced pressure to afford crude product, which was triturated with n-pentane (500 mL) to afford N-(2, 6-dimethylphenyl)-2-(piperidin-1-yl) butanamide (55 g) MS (ESI): m/z 275.27 [M+H]+. 1H NMR (400 MHz, DMSO-d₆) δ 9.16 (s, 1H), 7.06 (s, 3H), 3.06 (dd, J=5.7, 8.6 Hz, 1H), 2.60 (br t, J=4.8 Hz, 4H), 2.16 (s, 6H), 1.79-1.59 (m, 2H), 1.51 (br s, 4H), 1.44-1.35 (m, 2H), 0.93 (t, J=7.5 Hz, 3H).

Synthesis of 1-benzyl-1-(1-((2, 6-dimethylphenyl)amino)-1-oxobutan-2-yl) piperidin-1-ium Bromide To a stirred solution of N-(2,6-dimethylphenyl)-2-(piperidin-1-yl) butanamide (1.5 g, 5.5 mmol, 1.0 eq) in ACN (25.0 mL) was added benzyl bromide (1.872 g, 10.9 mmol, 2.0 eq) and the reaction mixture was heated to 80° C. for 16 h as progress of the reaction was monitored by TLC (mobile phase: 10% MeOH in DCM, visualization by UV). The reaction mixture was concentrated under reduced pressure and the crude product was triturated with EtOAc (3×10 mL) to afford 1-benzyl-1-(1-((2, 6-dimethylphenyl)amino)-1-oxobutan-2-yl)piperidin-1-ium bromide (1.2 g) MS (ESI): m/z 365.4 [M]. +. 1H NMR (400 MHz, DMSO-$d_6$) δ 10.36 (s, 1H), 7.57-7.54 (m, 5H), 7.17-7.11 (m, 3H), 5.41 (d, 1H), 4.62 (d, 1H), 4.39 (bs, 1H), 3.72 (bs, 2 H), 3.22 (bs, 2H), 2.43-2.39 (m, 1H), 2.15-2.07 (m, 9H), 1.96-1.95 (m, 2H), 1.61-1.45 (m, 2 H), 1.18 (t, 3H).

iv. Synthesis of 1-benzyl-1-(2-((2,6-dimethylphenyl)amino)-2-oxoethyl)azepan-1-ium Bromide

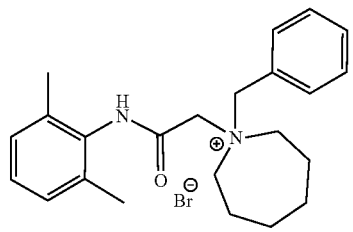 [SMILES: Cc1cccc(C)c1NC(=O)C[N+]1(Cc2ccccc2)CCCCCC1 ; [Cl-]]

Compound 4'A

Synthesis of Intermediate 2-(azepan-1-yl)-N-(2, 6-dimethylphenyl) acetamide

To a stirred solution of 2-bromo-N-(2, 6-dimethylphenyl) acetamide (0.5 g, 1.9 mmol, 1.0 eq) in ACN (5.0 mL) was added $K_2CO_3$ (0.639 g, 4.6 mmol, 2.5 eq) and azepane (0.4 mL, 4.0 mmol, 2.0 eq), and the mixture was stirred for 20 h at 90° C. as progress of the reaction was monitored by TLC (mobile phase: 5% MeOH in DCM, visualization by UV). The crude reaction was concentrated under reduced pressure and the resulting residue was partitioned between water and EtOAc (2×50 mL). The combined organic extracts were washed with brine solution, dried over $Na_2SO_4$, filtered and concentrated under reduced pressure to afford crude product, which was triturated with EtOAc (20 mL) to afford 2-(azepan-1-yl)-N-(2, 6-dimethylphenyl) acetamide (0.47 g). MS (ESI): m/z 261.57 [M+H]$^+$. 1H NMR (400 MHz, CHLOROFORM-d) δ 8.83 (br s, 1H), 7.09 (s, 3H), 3.32 (s, 2H), 2.93-2.73 (m, 4H), 2.24 (s, 6H), 1.87-1.52 (m, 9H).

Synthesis of 1-benzyl-1-(2-((2, 6-dimethylphenyl)amino)-2-oxoethyl) azepan-1-ium Bromide To a stirred solution of 2-(azepan-1-yl)-N-(2, 6-dimethylphenyl) acetamide (0.2 g, 0.8 mmol, 1.0 eq) in ACN (1.0 mL) was added benzyl bromide (0.1 mL, 0.6 mmol, 2.0 eq), and the reaction was heated to reflux for 16 has progress of the reaction was monitored by TLC (mobile phase: 10% MeOH in DCM, visualization by UV). The crude reaction mixture was concentrated under reduced pressure and the product was triturated with EtOAc (15 mL) to afford product 1-benzyl-1-(2-((2,6-dimethylphenyl)amino)-2-oxoethyl) azepan-1-ium bromide (0.12 g). MS (ESI): m/z 351.2 [M]$^+$. 1H NMR (400 MHz, DMSO-$d_6$) δ 10.04 (s, 1H), 7.71-7.62 (m, 2H), 7.60-7.48 (m, 3H), 7.20-7.03 (m, 3H), 4.93 (s, 2H), 4.15 (s, 2H), 3.86-3.70 (m, 2H), 3.66-3.42 (m, 2H), 2.23 (s, 6H), 1.98 (br d, J=4.8 Hz, 4H), 1.67 (br s, 4H).

v. Synthesis of 1-benzyl-1-(1-((2, 6-dimethylphenyl)amino)-1-oxobutan-2-yl) azepan-1-ium

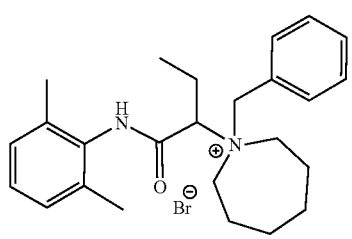 [SMILES: CCC(C(=O)Nc1c(C)cccc1C)[N+]1(Cc2ccccc2)CCCCCC1 ; [Cl-]]

Compound 5'A

Synthesis of Intermediate 2-(azepan-1-yl)-N-(2, 6-dimethylphenyl) butanamide

To a stirred solution of 2-bromo-N-(2, 6-dimethylphenyl) butanamide (0.5 g, 1.9 mmol, 1.0 eq) in ACN (10 mL) was added $K_2CO_3$ (0.393 g, 2.85 mmol, 1.5 eq) and azepane (0.376 g, 3.8 mmol, 2.0 eq), and the reaction mixture was stirred for 16 h at 75° C. as progress of the reaction was monitored by TLC (mobile phase: 10% MeOH in DCM, visualization by UV). The crude reaction mixture was quenched with water (10 mL) and extracted EtOAc (2×15 mL). The combined organic extracts were dried over $Na_2SO_4$, filtered and concentrated under reduced pressure to afford intermediate 2-(azepan-1-yl)-N-(2, 6-dimethylphenyl) butanamide (0.20 g). MS (ESI): m/z 289.33 [M+H]$^+$. 1H NMR (400 MHz, $CDCl_3$-d) δ ppm 1.00-1.16 (3H, m), 1.57-1.86 (12H, m), 1.95-2.13 (2H, m), 2.18-2.29 (8H, m), 2.72-2.97 (4H, m), 3.24 (1H, br t, J=6.72 Hz), 3.46-3.55 (2H, m), 7.03-7.15 (4H, m), 8.75 (1H, br s).

Synthesis of 1-benzyl-1-(1-((2, 6-dimethylphenyl)amino)-1-oxobutan-2-yl) azepan-1-ium Bromide To a stirred solution of 2-(azepan-1-yl)-N-(2, 6-dimethylphenyl) butanamide (0.2 g, 0.7 mmol, 1.0 eq) in ACN (5 mL) was added benzyl bromide (0.459 g, 2.85 mmol, 1.5 eq) and the reaction was stirred for 16 h at 75° C. as progress was monitored by TLC (mobile phase: 10% MeOH in DCM, visualization by UV). The reaction mixture was cooled to room temperature and concentrated under reduced pressure to afford crude product, which was triturated with EtOAc (20 mL) and dried under vacuo to afford 1-benzyl-1-(1-((2, 6-dimethylphenyl)amino)-1-oxobutan-2-yl) azepan-1-ium bromide (0.118 g). MS (ESI): m/z 379.52 [M]+. 1H NMR (500 MHz, DMSO-$d_6$) δ ppm 1.16 (3H, t, J=7.32 Hz), 1.26-1.51 (4H, m), 1.60 (2H, br s), 1.77-1.94 (2H, m), 2.10-2.31 (7H, m), 2.34-2.48 (1H, m), 3.56-3.81 (4H, m), 4.26 (1H, br d, J=10.68 Hz), 4.66 (1H, d, J=13.12 Hz), 5.21 (1H, d, J=13.12 Hz), 7.06-7.22 (3H, m), 7.45-7.61 (3H, m), 7.61-7.69 (2H, m), 10.42 (1H, s).

vi. Synthesis of 1-benzyl-1-(2-((2,6-dimethylphenyl)amino)-2-oxoethyl)azocan-1-ium Bromide

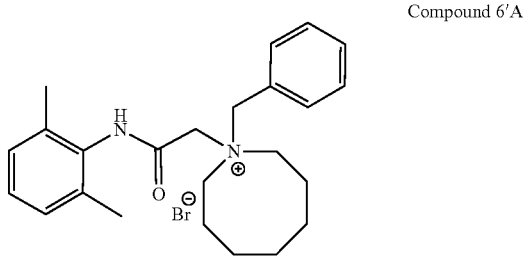 [SMILES: Cc1cccc(C)c1NC(=O)C[N+]1(Cc2ccccc2)CCCCCCC1 ; [Br-]]

Compound 6'A

Synthesis of Intermediate 2-(azocan-1-yl)-N-(2,6-dimethylphenyl) acetamide

To a stirred solution of 2-bromo-N-(2, 6-dimethylphenyl) acetamide (500 mg, 2.065 mmol) in ACN (5.0 mL) was added $K_2CO_3$ (713 mg, 5.159 mmol) followed by azocane (467 mg, 4.125 mmol) and the resulting reaction mixture was stirred for 16 h at 80° C. as progress of the reaction was monitored by TLC (5% MeOH in DCM, visualization by UV). The crude reaction mixture was poured into ice-cold water (40 mL) and extracted with EtOAc (2×50 mL). The combined organic extracts were washed with brine solution (50 mL), dried over anhydrous $Na_2SO_4$, and subsequently concentrated under reduced pressure to afford 2-(azocan-1-yl)-N-(2,6-dimethylphenyl) acetamide (480 mg) as an off white solid. Mass (ESI): m/z 275.1 [M+H]+. 1H NMR (400 MHz, CHLOROFORM-d) δ ppm 8.74 (br s, 1H), 7.02-7.16 (m, 3H), 3.34 (s, 2H), 2.74-2.88 (m, 4H), 2.25 (s, 6H), 1.53-1.80 (m, 10H).

Synthesis of 1-benzyl-1-(2-((2,6-dimethylphenyl)amino)-2-oxoethyl)azocan-1-ium Bromide To a stirred solution of 2-(azocan-1-yl)-N-(2, 6-dimethylphenyl) acetamide (200 mg, 0.728 mmol) in ACN (2.0 mL) was added benzyl bromide (240 mg, 1.403 mmol) and the resulting reaction mixture was stirred for 16 h at 90° C. as progress of the reaction was monitored by TLC (5% MeOH in DCM, visualization by UV). The reaction mixture was concentrated under reduced pressure to afford crude product which was triturated with a 1:1 mixture of EtOAc:Et2O (3×50 mL) to afford 1-benzyl-1-(2-((2, 6-dimethylphenyl)amino)-2-oxoethyl) azocan-1-ium bromide as a pale brown solid. Mass (ESI): m/z 365.54 [M]+. 1H NMR (400 MHz, DMSO-d6) δ ppm 10.02 (s, 1H), 7.46-7.70 (m, 5H), 7.05-7.22 (m, 3H), 4.89 (s, 2H), 4.07 (s, 2H), 3.64-3.76 (m, 2H), 3.48-3.62 (m, 2H), 2.23 (s, 6H), 1.94-2.14 (m, 4H), 1.50-1.83 (m, 6H).

Example 2—Inhibition of Nav1.7 Current

The compounds were synthesized according to the described methods and tested for the ability to inhibit voltage-gated sodium channels.

Cell Culture

NaV1.7 was expressed upon induction with tetracycline. Cells were cultured in DMEM containing 10% dialyzed Fetal Bovine Serum (VWR, Radnor, Pa.), 1% Glutamax (VWR, Radnor, Pa.), 1% Penicillin-Streptomycin (VWR, Radnor, Pa.), 100 mg/L Hygromycin (Thermo Fisher Scientific, Waltham, Mass. and 5 mg/L Blasticidin (Alfa Aesar, Haverhill, Mass.). Cells were grown and maintained at 37° C. in a humidified environment containing 10% $CO_2$ in air. Cells were detached from the culture flask for passage and harvested using 0.05% Trypsin-EDTA (Thermo Fisher Scientific, Waltham, Mass.). To induce NaV1.7, cells were induced with tetracycline (0.1-1 µg/mL, IBI Scientific, Peosta, Iowa) the day before recording and plated onto 24-well plates. Cells were washed with DPBS (VWR, Radnor, Pa.), trypsinized and then triturated five times in 10 mL of growth media to break apart cell aggregates. For one 24-well plate, 2 mL of cell suspension was mixed with 23 mL of fresh growth media and 0.1-1 µg/mL tetracycline added. 1 ml of mixed media with cells was then added to each well of a 24-well plate, with a 12 mm coverslip already placed in the bottom of the well. Cells were then incubated in 37° C. and 10% $CO_2$ overnight.

Patch Clamp Solutions & Drugs

The intracellular solution contained the following (in mM) CsCl 135, NaCl 10, EGTA 10, HEPES 10, $MgCl_2$ 2, adjusted to pH 7.2 with CsOH. The external solution was a normal Ringer solution containing (in mM) NaCl 155, HEPES 10, glucose 10, KCl 3.5, $CaCl_2$ 1.5, $MgCl_2$ 1 adjusted to pH 7.4 with NaOH. CsCl is from Alfa Aesar, Haverhill, Mass. All other chemicals are from Sigma-Aldrich, St. Louis, Mo. In order to test the degree of internal block by test compounds the compounds were dissolved in internal solution at the indicated test concentration. In control experiments the internal solution did not contain any compound. In order to test the degree of external block by test compounds the compounds were dissolved in external solution at the indicated test concentration.

Whole Cell Patch Clamp Protocol 18-24 hours after cells were induced with tetracycline, coverslips were placed into a chamber filled with Normal Ringer solution at room temperature and the chamber placed on a microscope. Pipettes were pulled from borosilicate glass on a P97 puller (Sutter Instrument, Novato, Calif.) and polished with a MF-830 Microforge (Narishige International USA, Inc, Amityville, N.Y.) to have a resistance of 1.5-2.5 MΩ when filled with CsCl internal solution at room temperature. Healthy cells (those that are round and translucent with no visible blemishes) were chosen for seal formation. A seal was formed between the pipette and the cell, and a brief pulse of suction was used to "break in" and establish the whole-cell configuration. The membrane potential was held at −100 mV before the voltage protocol began. Only cells with series resistance between 1.5-5 MΩ were retained for analysis. The voltage protocol was as follows: Cells were held at −100 mV for 12 ms followed by a hyperpolarizing step to −105 mV for 12 ms to monitor the leak. Cells were then stepped back to −100 mV for 40 ms. Cells were then depolarized to −20 mV for 10 ms and then returned to −100 mV for 26 ms (The FIGURE).

Internal Block by Test Compounds

Once the recording was started, the voltage protocol was run at 30 second intervals for 5 minutes to get a stable baseline. This was followed by four 30-second periods of 5 Hz stimulation of the same voltage protocol separated by 1 minute of rest which was then followed by 0.33 Hz stimulation after the last train. Currents were recorded using PatchMaster software with Heka EPC10 (HEKA Electronics, Lambrecht, Germany). Only cells with inward current amplitudes at −20 mV between 400 pA and 4 nA were accepted. In addition, cells having leak currents greater than 10% of their current amplitudes were discarded.

Data Analysis: Internal Block

The data was plotted using the Patchmaster software (HEKA Electronics, Lambrecht, Germany) and analyzed by plotting the minimum current during the voltage step to −20 mV (peak inward current) as a function of time. In order to determine the degree of rundown over the course of an experiment, the average peak inward current amplitude (2-3 points) before 5 Hz stimulation was designated as the baseline ($I_{baseline}$). The average peak inward current during the last 2 second of the last 5 Hz train was measured ($I_{test}$). The control fraction current remaining was calculated by dividing $I_{test}$ by $I_{baseline}$. On each recording day three cells were tested with control internal solution and the average fraction of current remaining calculated (Ctrl fraction current).

To determine the % block produced by test compounds applied internally the following was done. The average peak inward current amplitude (2-3 points) before 5 Hz stimulation was designated as 0% block ($I_{0\% \ block}$). To correct for the current change under control conditions, $I_{0\% \ block}$ was multiplied by the average Ctrl fraction current remaining to get the corrected 0% block current. The average peak inward current during the last 2 seconds of the last 5 Hz train was designated as the unblocked current ($I_{unblocked}$). The % block was calculated using the following equation: $(1-I_{unblocked}/(I_{0\% \ block}*\text{Ctrl fraction current remaining}))\times 100$. Compounds 1A' to 6A' (Example 1) were tested for intracellular inhibition of NaV 1.7. All of the compounds had a Nav1.7 intracellular inhibition in the range of ≥90% at a test concentration of 10 M.

External Block by Test Compounds

Once the recording was started, the voltage protocol was run at 30 second intervals for 5 minutes to get a stable baseline. This is followed by 5 Hz stimulation of the same voltage protocol run until the end of experiment. The test compound is added during the 5 Hz stimulation train making sure to wait until the cell shows stable current rundown rate before addition of the compound. The test compound is added for 5 minutes before washing out with normal Ringer's solution. Currents were recorded using PatchMaster software with Heka EPC10 (HEKA Electronics, Lambrecht, Germany). Only cells with inward current amplitudes at −20 mV between 400 pA and 4 nA were accepted. In addition, cells having leak currents greater than 10% of their current amplitudes were discarded.

Data Analysis: External Block

The data was plotted using the Patchmaster software (HEKA Electronics, Lambrecht, Germany) and analyzed by plotting the minimum current during the voltage step to −20 mV (peak inward current) as a function of time. To determine the % block produced by test compounds applied externally the following was done. After the stable current rundown rate was established during the 5 Hz stimulation train, the $\text{Rate}_{rundown}$ was calculated by dividing the change in peak current amplitude by time. The average peak inward current amplitude (2-3 seconds) before addition of compound was used to determine 0% block ($I_{0\% \ block}$). To correct for the rundown, $I_{0\% \ block}$ is subtracted by the ($\text{Rate}_{rundown}*5$ min) to get the corrected 0% block current. The average peak inward current during the last 2-3 seconds of the 5 minutes of compound application time before washing is the unblocked current ($I_{unblocked}$). The % block was then calculated using the following equation: Fraction current block=$1-I_{unblocked}/(I_{0\% \ block}-\text{Rate}_{rundown}*5 \text{ min})$.

Compounds 1A' to 4A' were tested for extracellular inhibition of NaV 1.7. Compounds 1A', 2A', 3A', and 4A' had a Nav1.7 extracellular inhibition in the range of <40% at a test concentration of 10 M.

Example 3—Membrane Permeability

The PAMPA assay (pION, Inc., Woburn Mass.) was used to determine the ability of compounds of the invention to cross an artificial lipid membrane by passive diffusion. Test compounds were dissolved in DMSO (10 mM) and diluted 200-fold in buffer (pION Inc., pH 7.4) to provide 50 uM stock solutions. Buffer (150 μL) was added to a UV blank plate and stock solutions (150 μL) were transferred to a UV reference plate. The blank and reference spectrum were read using a spectrophotometer. Stock solutions (200 μL) were added to the donor plate of the PAMPA sandwich plate and an accept plate painted with GIT lipid (pION Inc, 5 μL) was placed on top. Buffer (200 μL) was added to the acceptor plate and the PAMPA sandwich plate was incubated for 4 hours. Aliquots (150 μL) from the acceptor plate were added to a UV plate and read as acceptor spectrum. Aliquots (150 μL) of the donor solutions were added to a UV analysis plate and read as donor spectrum. The permeability coefficient of test compounds was calculated using PAMPA Explorer™ software (version 3.5.0.4) based on the AUC of the reference plate, the donor plate, and the acceptor plate.

The PAMPA permeability results for each of Compounds 2A', 3A', 4A', 5A' and 6'A were <1 $10^{-6}$ cm/s.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

What is claimed is:

1. A compound represented by Formula (I):

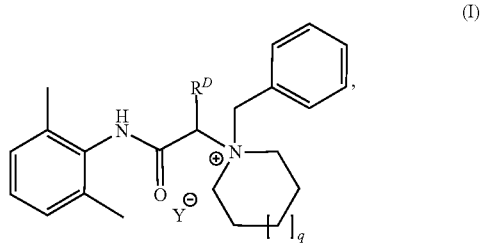

wherein:

$Y^-$ is a pharmaceutically acceptable anion;

q is 0, 1, 2, or 3; and $R^D$ is hydrogen, methyl, or ethyl.

2. The compound of claim 1, wherein q is 0.

3. The compound of claim 2, wherein $R^D$ is hydrogen or ethyl.

4. The compound of claim 1, wherein q is 1.

5. The compound of claim 4, wherein $R^D$ is hydrogen or ethyl.

6. The compound of claim 1, wherein q is 2.

7. The compound of claim 6, wherein $R^D$ is hydrogen or ethyl.

8. The compound of claim 1, wherein q is 3.

9. The compound of claim 8, wherein $R^D$ is hydrogen or ethyl.

10. The compound of claim 1, wherein the compound is:

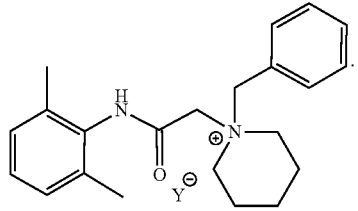

11. The compound of claim 1, wherein the compound is:

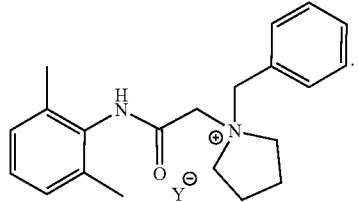

12. The compound of claim 1, wherein the compound is:

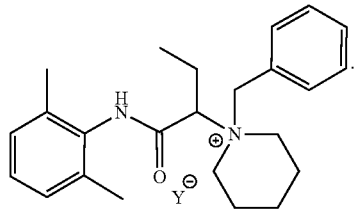

13. The compound of claim 1, wherein the compound is:

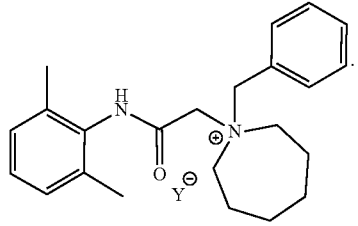

14. The compound of claim 1, wherein the compound is:

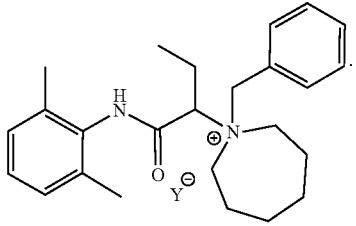

15. The compound of claim 1, wherein the compound is:

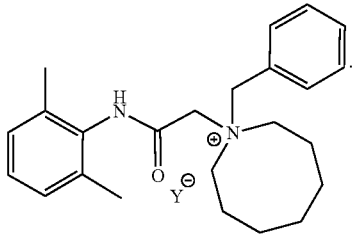

16. The compound of claim 10, wherein Y– is bromide or chloride.

17. The compound of claim 11, wherein Y– is bromide or chloride.

18. The compound of claim 12, wherein Y– is bromide or chloride.

19. The compound of claim 13, wherein Y– is bromide or chloride.

20. The compound of claim 14, wherein Y– is bromide or chloride.

21. The compound of claim 15, wherein Y– is bromide or chloride.

22. A pharmaceutical composition comprising the compound of claim 1 or a pharmaceutically acceptable salt thereof, and a pharmaceutically acceptable excipient.

23. The composition of claim 22, wherein said composition is formulated for oral, intravenous, intramuscular, rectal, cutaneous, subcutaneous, topical, transdermal, sublingual, nasal, inhalation, vaginal, intrathecal, epidural, or ocular administration.

24. A method for treating pain, cough, itch, or a neurogenic inflammatory disorder in a patient, comprising administering to said patient an effective amount of the compound of claim 1.

25. The method of claim 24, wherein said pain is selected from the group consisting of pain due to back and neck pain, lower back pain, cancer pain, gynecological and labor pain, fibromyalgia, arthritis, rheumatoid arthritis, osteoarthritis, rheumatological pains, orthopedic pains, acute and post herpetic neuralgia and other neuropathic pains, sickle cell crises, vulvodynia, peri-anal pain, irritable bowel disease, irritable bowel syndrome, inflammatory bowel disease, oral mucositis, esophagitis, interstitial cystitis, urethritis and other urological pains, dental pain, headaches, trigeminal trophic syndrome, erythromelalgia, abdominal wall pain, chronic abdominal wall pain, allergic rhinitis, muscle pain, rectal pain, Levator ani syndrome, proctalgia fugax, hemorrhoid pain, stomach pain, skin ulcers, stomach ulcers, burn pain, ophthalmic irritation, conjunctivitis, eye redness, dry eye, dry eye syndrome, complex regional pain syndrome, post-surgical ocular pain, postoperative pain, acute postoperative pain, and procedural pain, draining an abscess, surgery, dental procedures, ophthalmic procedures, ophthalmic irritation, conjunctivitis, eye redness, dry eye, arthroscopies and use of other medical instrumentation, cosmetic surgical procedures, dermatological procedures, setting fractures, and biopsies.

26. The method of claim 24, wherein said cough is selected from the group consisting of cough in patients with asthma, COPD, asthma-COPD overlap syndrome (ACOS), interstitial pulmonary fibrosis (IPF), idiopathic pulmonary fibrosis, post viral cough, post-infection cough, chronic idiopathic cough, and lung cancer.

27. The method of claim 24, wherein said itch is selected from the group consisting of itch due to pruritus, brachioradial pruritus, chronic idiopathic pruritus, genital/anal pruritus, notalgia paresthetica, scalp pruritus, allergic dermatitis, contact dermatitis, atopic dermatitis, hand eczema, poison ivy, infections, parasites, insect bites, pregnancy, metabolic disorders, liver or renal failure, drug reactions, allergic reactions, eczema, genital and anal itch, hemorrhoid itch, and cancer.

28. The method of claim 24, wherein said neurogenic inflammatory disorder is selected from the group consisting of allergic inflammation, asthma, chronic cough, conjunctivitis, rhinitis, psoriasis, inflammatory bowel disease, interstitial cystitis, arthritis, colitis, contact dermatitis, diabetes, eczema, cystitis, gastritis, migraine headache, rosacea, sunburn, pancreatitis, chronic rhinosinusistis, traumatic brain injury, polymicrobial sepsis, tendinopathies, chronic urticaria, rheumatic disease, acute lung injury, exposure to irritants, inhalation of irritants, pollutants, chemical warfare agents, and atopic dermatitis.

* * * * *